US010508166B2

(12) United States Patent
Holtcamp et al.

(10) Patent No.: US 10,508,166 B2
(45) Date of Patent: Dec. 17, 2019

(54) PRODUCTION OF POLYOLEFINS WITH INTERNAL UNSATURATION STRUCTURES USING A METALLOCENE CATALYST SYSTEM

(71) Applicant: ExxonMobil Chemical Patents Inc., Baytown, TX (US)

(72) Inventors: Matthew W. Holtcamp, Huffman, TX (US); Matthew S. Bedoya, Humble, TX (US); Xuan Ye, Houston, TX (US); David F. Sanders, Beaumont, TX (US); Gregory S. Day, College Station, TX (US); Sarah J. Mattler, League City, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 15/893,922

(22) Filed: Feb. 12, 2018

(65) Prior Publication Data
US 2018/0162973 A1 Jun. 14, 2018

Related U.S. Application Data

(62) Division of application No. 15/249,021, filed on Aug. 26, 2016, now Pat. No. 9,926,396.

(60) Provisional application No. 62/245,603, filed on Oct. 23, 2015.

(51) Int. Cl.
*C08F 4/6592* (2006.01)
*C08F 210/02* (2006.01)
*C08F 210/16* (2006.01)
*C07F 7/08* (2006.01)
*C08F 4/659* (2006.01)

(52) U.S. Cl.
CPC .......... *C08F 210/16* (2013.01); *C07F 7/0803* (2013.01); *C08F 4/65927* (2013.01); *C08F 210/02* (2013.01); *C08F 4/65912* (2013.01); *C08F 4/65916* (2013.01); *C08F 4/65925* (2013.01); *C08F 2500/12* (2013.01); *C08F 2500/18* (2013.01); *C08F 2800/20* (2013.01)

(58) Field of Classification Search
CPC .............. C08F 4/65908; C08F 4/65912; C08F 4/65925; C08F 4/65927; C08F 210/02; C08F 210/16
See application file for complete search history.

(56) References Cited

U.S. PATENT DOCUMENTS

| 3,513,152 | A | 5/1970 | Hogan |
| 5,767,208 | A | 6/1998 | Turner |
| 6,242,545 | B1 | 6/2001 | Jejelowo et al. |
| 6,569,965 | B2 | 5/2003 | Markel et al. |
| 6,730,756 | B1 | 5/2004 | Andell et al. |
| 6,936,675 | B2 | 8/2005 | Szul et al. |
| 6,956,088 | B2 | 10/2005 | Farley et al. |
| 7,157,531 | B2 | 1/2007 | Szul et al. |
| 7,285,608 | B2 | 10/2007 | Schottek et al. |
| 8,299,287 | B2 | 10/2012 | Dimeska et al. |
| 8,623,974 | B2 | 1/2014 | Jiang et al. |
| 8,969,482 | B2 | 3/2015 | Stewart |
| 2005/0153830 | A1 | 7/2005 | Jensen et al. |
| 2007/0043176 | A1 | 2/2007 | Martin et al. |
| 2007/0073013 | A1 | 3/2007 | Razavi |
| 2008/0038533 | A1 | 2/2008 | Query |
| 2009/0318644 | A1 | 12/2009 | Brant et al. |
| 2010/0292421 | A1 | 11/2010 | Bando |
| 2014/0087987 | A1 | 3/2014 | Crowther et al. |

FOREIGN PATENT DOCUMENTS

WO 2003/027131 4/2003

OTHER PUBLICATIONS

Karttunen et al., "The Influence of the Ligand Structure on Activation of Hafnocene Polymerization Catalysts: A Theoretical Study", Journal of Organometallic Chemistry, vol. 693, 2008, pp. 155-163.
Karttunen et al., "Influence of the Ligand Structure of Hafnocene Polymerization Catalysts: A Theoretical Study on Ethene Insertion and Chain Propagation", Organometallics, 2008, vol. 27, pp. 3390-3398.
Karttunen et al., "Influence of the Ligand Structure of Hafnocene Polymerization Catalysts: A Theoretical Study on Chain Termination Reactions in Ethene Polymerization", Journal of Organometallic Chemistry, vol. 693, 2008, pp. 3915-3922.
Busico et al., "1H NMR Analysis of Chain Unsaturations in Ethylene/1-Octene Copolymers Prepared with Metallocene Catalysts at High Temperature", Macromolecules, 2005, vol. 38 (16), pp. 6988-6996.
He et al., "Terminal and Internal Unsaturations in Poly(ethylene-co-1-octane)", Macromolecules, 2014, vol. 47, pp. 3782-3790.

*Primary Examiner* — Caixia Lu
(74) *Attorney, Agent, or Firm* — Catherine L. Bell

(57) ABSTRACT

This invention relates to a process to polymerize olefins, particularly to produce ethylene polymers with internal unsaturation structures.

34 Claims, 2 Drawing Sheets

PRODUCTION OF POLYOLEFINS WITH INTERNAL UNSATURATION STRUCTURES USING A METALLOCENE CATALYST SYSTEM

CROSS REFERENCE TO RELATED APPLICATIONS

This application is a divisional of U.S. Ser. No. 15/249,021, filed Aug. 26, 2016, which claims priority to and the benefit of U.S. Ser. No. 62/245,603, filed Oct. 23, 2015.

FIELD OF THE INVENTION

This invention relates to a process to polymerize olefins, particularly to produce ethylene polymers with internal unsaturation structures.

BACKGROUND OF THE INVENTION

Olefin polymerization catalysts are of great use in industry. Hence, there is interest in finding new catalyst systems that increase the commercial usefulness of the catalyst and allow the production of polymers having improved properties.

Catalysts for olefin polymerization are often based on hafnocenes as catalyst precursors, which are activated either with the help of an alumoxane, or with an activator containing a non-coordinating anion. For example, U.S. Pat. No. 7,157,531 discloses bis(n-propyl Cp)Hf Me$_2$ catalyst compounds used to make ethylene polymer having a controlled comonomer distribution.

Other references of interest include: U.S. Pat. Nos. 6,242,545; 6,956,088; US 2008/0038533; U.S. Pat. No. 6,936,675; Macromolecules 2005, vol. 38, p. 6988; and Macromolecules 2014, vol. 47, p. 3782.

However, it is a need in the art to develop a new process for the polymerization of olefins and improved catalyst systems suitable for the process, in order to achieve specific and balanced polymer properties, including high molecular weight, increased comonomer incorporation, low content of long chain branching and high internal unsaturation structures within the backbone of polymers.

SUMMARY OF THE INVENTION

This invention relates to a process to polymerize olefins comprising:
1) contacting olefin monomers with a catalyst system comprising an activator and a bis-cyclopentadienyl metallocene compound represented by the formula:

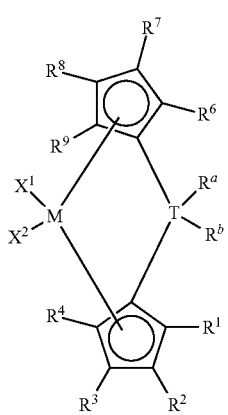

wherein:
M is Hf;
each $X^1$ and $X^2$ is, independently, a hydrocarbyl radical having from 1 to 20 carbon atoms, hydride, amide, alkoxide, sulfide, phosphide, halide, diene, amine, phosphine, ether, or $X^1$ and $X^2$ may form a part of a fused ring or a ring system; each of $R^1$, $R^2$, $R^3$, $R^4$, $R^6$, $R^7$, $R^8$, and $R^9$ is, independently, hydrogen, halide, alkoxide or a $C_1$ to $C_{40}$ (preferably $C_1$ to $C_{20}$) substituted or unsubstituted hydrocarbyl group, provided that at least one of $R^1$, $R^2$, $R^3$, $R^4$, $R^6$, $R^7$, $R^8$, and $R^9$, is a linear $C_3$ to $C_{20}$ substituted or unsubstituted hydrocarbyl group;
T is a group 14 atom (preferably, silicon or germanium; more preferably, silicon); each $R^a$ and $R^b$ is, independently, a $C_1$ to $C_{40}$ substituted or unsubstituted hydrocarbyl, (preferably a $C_1$ to $C_{20}$ substituted or unsubstituted alkyl, or a $C_6$ to $C_{20}$ substituted or unsubstituted aryl (such as phenyl, and substituted phenyl groups);
wherein the bis-cyclopentadienyl metallocene compound generates hydrogen and the polymerization occurs in the presence of hydrogen, preferably at least 200 ppm hydrogen; and
2) obtaining a polymer having:
  a) an internal unsaturation of 50% or more;
  b) a melt index of 20 dg/min or less; and
  c) a g'vis of 0.95 or more.

This invention further relates to a catalyst system comprising an activator and the bis-cyclopentadienyl metallocene compound represented by the above formula herein.

This invention further relates to a polymer produced by the process described herein, wherein the polymer has: a) an internal unsaturation of 50% or more; b) a melt index of 20 dg/min or less; and c) a g'vis of 0.95 or more.

This invention further relates to an ethylene polymer produced by the process described herein, wherein the polymer has: a) an internal unsaturation of 60% or more, b) a melt index of 1.0 dg/min or less; and c) a g'vis of 0.95 or more.

The inventors interestingly found that the produced polymer has a combination of high Mw capability, improved hexene response, low content of long chain branching, and particularly high levels of internal unsaturation structures.

DETAILED DESCRIPTION OF THE INVENTION

Figure 1:
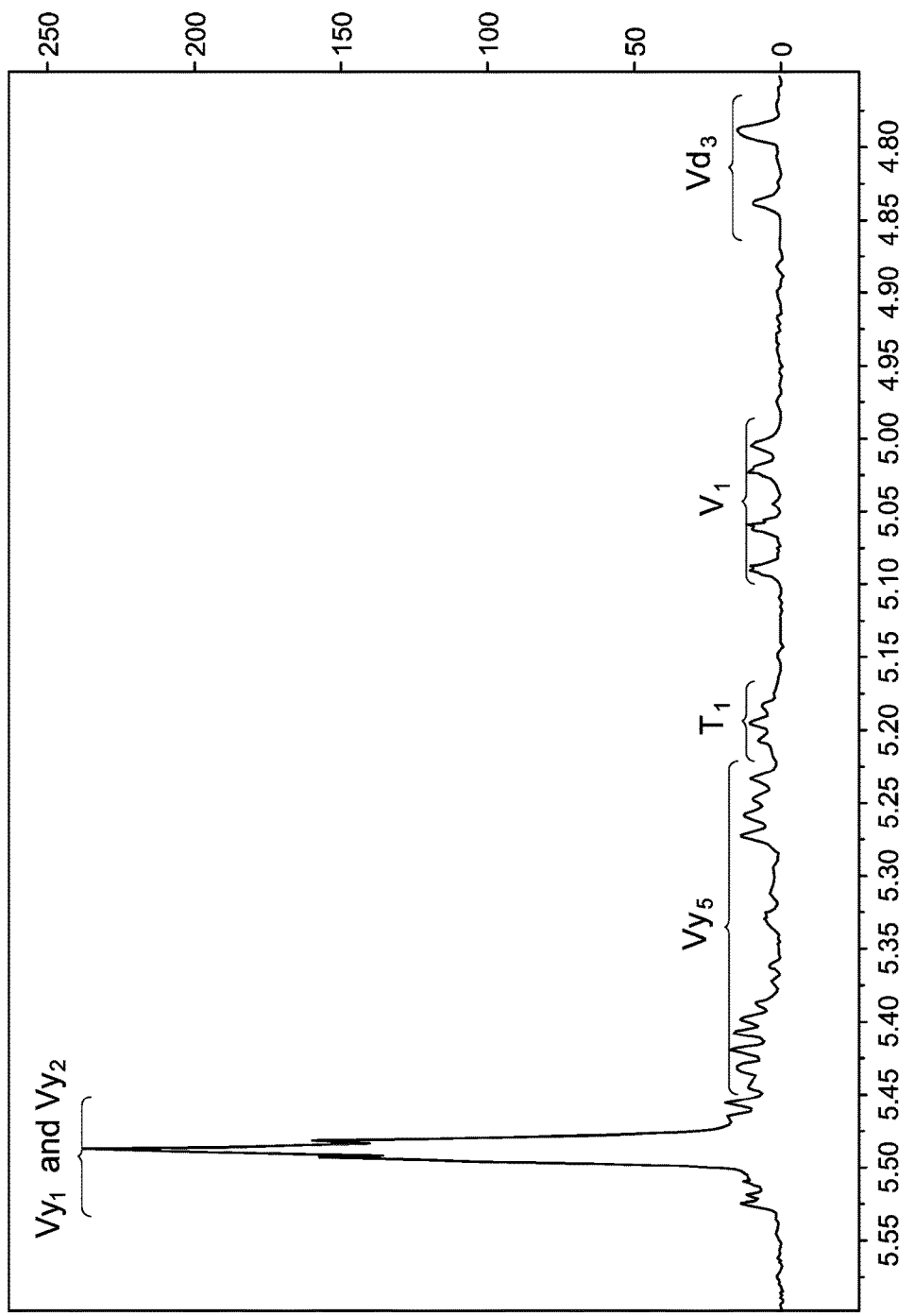
FIG. 1 is the $^1$H NMR spectra of the olefinic region of the polymer made using supported Catalyst B in Table 1.
Figure 2:
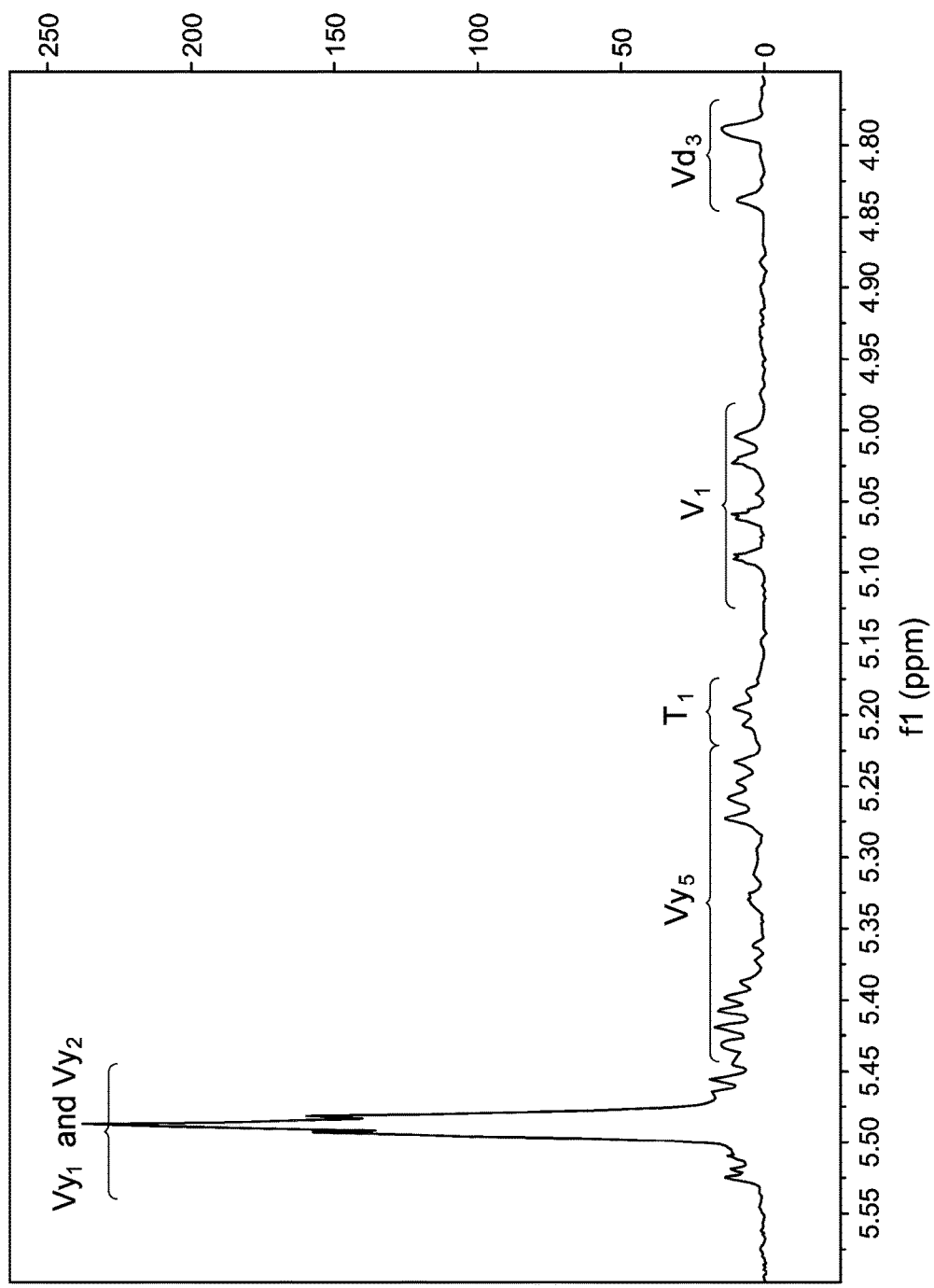
FIG. 2 is the $^1$H NMR spectra of the olefinic region of the polymer made using supported Catalyst A in Table 1.

For the purposes of this invention and the claims thereto, the new numbering scheme for the Periodic Table Groups is used as described in CHEMICAL AND ENGINEERING NEWS, vol. 63(5), p. 27, (1985). Therefore, a "group 4 metal" is an element from group 4 of the Periodic Table, e.g., Hf, Ti, or Zr.

"Catalyst productivity" is a measure of how many grams of polymer (P) are produced using a polymerization catalyst comprising W g of catalyst (cat), over a period of time of T hours; and may be expressed by the following formula: P/(T×W) and expressed in units of gPgcat$^{-1}$ hr$^{-1}$. Conversion is the amount of monomer that is converted to polymer product, and is reported as mol % and is calculated based on the polymer yield and the amount of monomer fed into the reactor. Catalyst activity is a measure of how active the catalyst is and is reported as the mass of product polymer (P) produced per mole of catalyst (cat) used (kgP/molcat).

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, and so on.

For the purposes of this invention, ethylene shall be considered an α-olefin.

For the purposes of this invention and claims thereto, the term "substituted" means that a hydrogen group has been replaced with a heteroatom, or a heteroatom-containing group.

As used herein, Mn is number average molecular weight, Mw is weight average molecular weight, and Mz is z average molecular weight, wt % is weight percent, and mol % is mole percent. Molecular weight distribution (MWD), also referred to as polydispersity (PDI), is defined to be Mw divided by Mn. Unless otherwise noted, all molecular weight units (e.g., Mw, Mn, Mz) are g/mol. The following abbreviations may be used herein: Me is methyl, Et is ethyl, Pr is propyl, cPR is cyclopropyl, nPr is n-propyl, iPr is isopropyl, Bu is butyl, nBu is normal butyl, iBu is isobutyl, sBu is sec-butyl, tBu is tert-butyl, Oct is octyl, Ph is phenyl, Bn is benzyl, and MAO is methylalumoxane.

A "catalyst system" is a combination of at least one catalyst compound, at least one activator, an optional co-activator, and an optional support material. For the purposes of this invention and the claims thereto, when catalyst systems are described as comprising neutral stable forms of the components, it is well understood by one of ordinary skill in the art that the ionic form of the component is the form that reacts with the monomers to produce polymers.

In the description herein, the metallocene compound may be described as a catalyst precursor, a pre-catalyst compound, catalyst compound or a transition metal compound, and these terms are used interchangeably. A metallocene catalyst is defined as an organometallic compound with two π-bound cyclopentadienyl moieties or substituted cyclopentadienyl moieties.

For purposes of this invention and claims thereto, in relation to metallocene compounds, the term "substituted" means that a hydrogen group has been replaced with a hydrocarbyl group, a heteroatom, or a heteroatom-containing group. For example, methyl cyclopentadiene (Cp) is a Cp group substituted with a methyl group.

Room temperature (RT) is 23° C. unless otherwise indicated.

For purposes of this disclosure, "hydrocarbyl radical" is defined to be $C_1$-$C_{100}$ radicals, that may be linear, branched, or cyclic, and when cyclic, aromatic or non-aromatic. Examples of such radicals include, but are not limited to, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues. Substituted hydrocarbyl radicals are radicals in which at least one hydrogen atom of the hydrocarbyl radical has been substituted with at least one heteroatom or heteroatom-containing group (i.e., halogen (such as Br, Cl, F or I) or a functional group such as $NR*_2$, $OR*$, $SeR*$, $TeR*$, $PR*_2$, $AsR*_2$, $SbR*_2$, $SR*$, $BR*_2$, $SiR*_3$, $GeR*_3$, $SnR*_3$, $PbR*_3$, and the like), or where at least one heteroatom has been inserted within a hydrocarbyl ring.

The term "aryl" or "aryl group" means a six carbon aromatic ring and the substituted variants thereof, including but not limited to, phenyl, 2-methyl-phenyl, xylyl, 4-bromo-xylyl. Likewise, heteroaryl means an aryl group where a ring carbon atom (or two or three ring carbon atoms) has been replaced with a heteroatom, preferably N, O, or S. As used herein, the term "aromatic" also refers to pseudoaromatic heterocycles, which are heterocyclic substituents that have similar properties and structures (nearly planar) to aromatic heterocyclic ligands, but are not by definition aromatic; likewise the term aromatic also refers to substituted aromatics.

Reference to a hydrocarbyl, alkyl or aryl group without specifying a particular isomer (e.g., butyl) expressly discloses all isomers (e.g., n-butyl, iso-butyl, sec-butyl, and tert-butyl).

"Complex" as used herein, is also often referred to as catalyst precursor, pre-catalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

The term "continuous" means a system that operates without interruption or cessation. For example, a continuous process to produce a polymer would be one where the reactants are continually introduced into one or more reactors and polymer product is continually withdrawn.

Process

This invention relates to a process to polymerize olefins comprising:

1) contacting olefin monomers (such as ethylene and, optionally, a $C_3$ to $C_{12}$ comonomer (e.g., propylene, butene, hexene, and/or octene)) with a catalyst system comprising an activator (such as an alumoxane or a non-coordinating anion) and a bis-cyclopentadienyl metallocene compound represented by the formula:

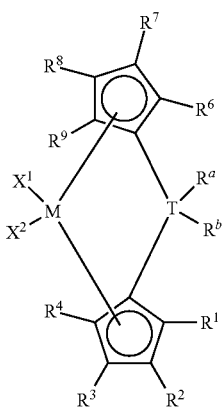

wherein:
M is Hf;
each $X^1$ and $X^2$ is, independently, a hydrocarbyl radical having from 1 to 20 carbon atoms, hydride, amide, alkoxide, sulfide, phosphide, halide, diene, amine, phosphine, ether, or $X^1$ and $X^2$ may form a part of a fused ring or a ring system; each of $R^1$, $R^2$, $R^3$, $R^4$, $R^6$, $R^7$, $R^8$, and $R^9$ is, independently, hydrogen, halide, alkoxide or a $C_1$ to $C_{40}$ substituted or unsubstituted hydrocarbyl group, (preferably, each of $R^1$, $R^2$, $R^3$, $R^4$, $R^6$, $R^7$, $R^8$, and $R^9$ is, independently, a $C_1$ to $C_{20}$ substituted or unsubstituted hydrocarbyl group), provided that at least one of $R^1$, $R^2$, $R^3$, $R^4$, $R^6$, $R^7$, $R^8$, and $R^9$ is a linear $C_3$ to $C_{20}$ substituted or unsubstituted hydrocarbyl group, (preferably at least one of $R^6$, $R^7$, $R^8$, and $R^9$ and at least one of $R^1$, $R^2$, $R^3$, $R^4$, is a linear $C_3$ to $C_{20}$ substituted or unsubstituted hydrocarbyl group, preferably at least one of $R^2$, $R^3$, $R^7$ and $R^8$ is a $C_3$ to $C_{10}$ linear alkyl group);
T is a group 14 atom (preferably, silicon or germanium; more preferably, silicon);
each $R^a$ and $R^b$ is, independently, a hydrocarbyl or a substituted hydrocarbyl, (preferably a substituted or unsubstituted $C_1$ to $C_{40}$ alkyl, or a $C_6$ to $C_{20}$ substituted or unsubstituted aryl preferably, each $R^a$ and $R^b$ is, independently, selected from the group consisting of substituted or unsubstituted $C_1$ to $C_{20}$ alkyl, phenyl, and substituted phenyl groups);
wherein the bis-cyclopentadienyl metallocene compound generates hydrogen and the polymerization occurs in the presence of hydrogen, preferably at least 200 ppm hydrogen; and
2) obtaining a polymer having:
    a) internal unsaturations of 50% or more;
    b) a melt index of 20 dg/min or less, preferably 1.0 or less; and
    c) a g'vis of 0.95 or more.

Advantageously, the metallocene catalyst (as activated in the catalyst system) produces hydrogen during the polymerization reaction. Hydrogen production is determined by measuring the amount of hydrogen present in a polymerization reaction where no hydrogen has been added to the reaction. The polymerization occurs in the presence of hydrogen, preferably at least 200 ppm hydrogen is present in the polymerization reaction, preferably at least 400 ppm, preferably at least 600 ppm. Alternately, hydrogen is present in the polymerization reactor at a partial pressure of 0.007 to 345 kPa, preferably from 0.07 to 172 kPa, preferably 0.7 to 70 kPa. Some or all of the hydrogen may be generated by the catalyst system. Even though the metallocene catalyst produces hydrogen, extra hydrogen may be added to the polymerization reaction.

Bis-Cyclopentadienyl Metallocene Compounds
As used herein, the bis-cyclopentadienyl metallocene compounds useful herein are represented by the formula:

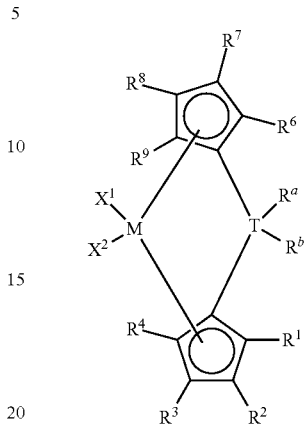

wherein:
M is Hf;
each $X^1$ and $X^2$ is, independently, a hydrocarbyl radical having from 1 to 20 carbon atoms, hydride, amide, alkoxide, sulfide, phosphide, halide, diene, amine, phosphine, ether, or $X^1$ and $X^2$ may form a part of a fused ring or a ring system; each of $R^1$, $R^2$, $R^3$, $R^4$, $R^6$, $R^7$, $R^8$, and $R^9$ is, independently, hydrogen, halide, alkoxide or a $C_1$ to $C_{40}$ substituted or unsubstituted hydrocarbyl group, (preferably, each of $R^1$, $R^2$, $R^3$, $R^4$, $R^6$, $R^7$, $R^8$, and $R^9$ is, independently, a $C_1$ to $C_{20}$ substituted or unsubstituted hydrocarbyl group) provided that at least one (preferably at least two) of $R^1$, $R^2$, $R^3$, $R^4$, $R^6$, $R^7$, $R^8$, and $R^9$ is a linear $C_3$ to $C_{20}$ substituted or unsubstituted hydrocarbyl group; preferably at least one of $R^2$ and $R^3$ and at least one of $R^7$ and $R^8$ is a $C_3$ to $C_{10}$ linear alkyl group, preferably a n-propyl, n-butyl, n-pentyl, n-hexyl, n-heptyl, n-octyl, n-nonyl, or n-decyl group;
T is a group 14 atom (preferably, silicon or germanium; more preferably, silicon); and
each $R^a$ and $R^b$ is, independently, a hydrocarbyl or a substituted hydrocarbyl, (preferably a substituted or unsubstituted $C_1$ to $C_{20}$ alkyl, a $C_6$ to $C_{20}$ substituted or unsubstituted aryl preferably, each $R^a$ and $R^b$ is, independently, selected from the group consisting of substituted or unsubstituted $C_1$ to $C_{12}$ alkyl groups and phenyl and substituted phenyl groups).

In any embodiment described herein, each $X^1$ and $X^2$ is, independently, selected from the group consisting of: Cl, Br, I, methyl, ethyl, propyl, butyl, pentyl, heptyl, octyl, nonyl, decyl, undecyl, dodecyl, and isomers thereof;

In any embodiment described herein, $R^1$, $R^2$, $R^3$, $R^4$, $R^6$, $R^7$, $R^8$, and $R^9$ is, independently, hydrogen, methyl, ethyl, propyl, butyl, pentyl, heptyl, octyl, nonyl, decyl, undecyl, dodecyl, or an isomer thereof, provided that at least one of $R^1$, $R^2$, $R^3$, $R^4$, $R^6$, $R^7$, $R^8$, and $R^9$ (preferably at least one of $R^2$, $R^3$, $R^7$ and $R^8$, preferably at least one of $R^2$ and $R^3$ and at least one of $R^7$ and $R^8$) is, independently, n-propyl, n-butyl, n-pentyl, n-hexyl, n-heptyl, n-octyl, n-nonyl, or n-decyl.

In any embodiment described herein, at least one of $R^2$ and $R^3$ and at least one of $R^7$ and $R^8$, is a $C_3$ to $C_{10}$ linear alkyl group, preferably a n-propyl, n-butyl, n-pentyl, n-hexyl, n-heptyl, n-octyl, n-nonyl, or n-decyl group.

In any embodiment described herein, at least one of $R^6$, $R^7$, $R^8$, and $R^9$ and at least one of $R^1$, $R^2$, $R^3$, $R^4$, is a linear $C_3$ to $C_{20}$ substituted or unsubstituted hydrocarbyl group, preferably a $C_3$ to $C_{10}$ linear alkyl group, preferably a n-propyl, n-butyl, n-pentyl, n-hexyl, n-heptyl, n-octyl, n-nonyl, or n-decyl group.

In any embodiment described herein, T is silicon.

Examples of $C_6$ to $C_{20}$ substituted or unsubstituted aryl groups include phenyl, benzyl, tolyl, carbazolyl, naphthyl, and the like.

In any embodiment described herein, each $R^a$ and $R^b$ is, independently, methyl, ethyl, propyl, butyl, pentyl, heptyl, octyl, nonyl, decyl, undecyl, dodecyl, phenyl, methyl phenyl, ethylphenyl, propylphenyl, butylphenyl, pentylphenyl, hexylphenyl, heptylphenyl, octylphenyl, nonylphenyl, decylphenyl, undecylphenyl, dodecylphenyl, phenylphenyl, or an isomer thereof.

In any embodiment described herein, each $R^a$ and $R^b$ is, independently, a phenyl group substituted with 1, 2, 3, 4, or 5 groups, preferably groups independently selected from the group consisting of: phenyl, methyl, ethyl, propyl, butyl, pentyl, heptyl, octyl, nonyl, decyl, undecyl, dodecyl, methyl phenyl, ethylphenyl, propylphenyl, butylphenyl, pentylphenyl, hexylphenyl, heptylphenyl, octylphenyl, nonylphenyl, decylphenyl, undecylphenyl, dodecylphenyl, phenylphenyl, and isomers thereof.

In any embodiment described herein, each $R^a$ and/or $R^b$ may be independently selected from the group consisting of phenyl, methyl phenyl, ethylphenyl, propylphenyl, butylphenyl, pentylphenyl, hexylphenyl, heptylphenyl, octylphenyl, nonylphenyl, decylphenyl, undecylphenyl, dodecylphenyl, phenylphenyl, fluorophenyl, chlorophenyl, bromophenyl, methoxyphenyl, trifluoromethylphenyl, dimethylaminophenyl, trimethylsilylphenyl, triethylsilylphenyl, tripropylsilylphenyl, (trimethylsilyl)ethylphenyl, 3,5-di(isopropyl)phenyl, 3,5-di(isobutyl)phenyl, 3,5-di(tert-butyl)phenyl, carbazol-9-yl, 3,6-di-tert-butylcarbazol-9-yl, 2,3,4,5,6,7,8,9-octahydrocarbazol-1-yl, anthracen-9-yl, 1,2,3,4,5,6,7,8-octahydroanthracen-9-yl, naphthyl, fluoren-9-yl, 9-methylfluoren-9-yl, 1,2,3,4,5,6,7,8-octahydrofluoren-9-yl, or 9-methyl-1,2,3,4,5,6,7,8-octahydrofluoren-9-yl, and isomers thereof.

In any embodiment described herein, at least one of $R^6$, $R^7$, $R^8$, and $R^9$ and at least one of $R^1$, $R^2$, $R^3$, $R^4$, is a linear $C_3$ to $C_{20}$ substituted or unsubstituted hydrocarbyl group, preferably a $C_3$ to $C_{10}$ linear alkyl group, preferably a n-propyl, n-butyl, n-pentyl, n-hexyl, n-heptyl, n-octyl, n-nonyl, or n-decyl group and each $R^a$ and $R^b$ is, independently, methyl, ethyl, propyl, butyl, pentyl, heptyl, octyl, nonyl, decyl, undecyl, dodecyl, phenyl, methyl phenyl, ethylphenyl, propylphenyl, butylphenyl, pentylphenyl, hexylphenyl, heptylphenyl, octylphenyl, nonylphenyl, decylphenyl, undecylphenyl, dodecylphenyl, phenylphenyl, or an isomer thereof.

In some preferred embodiments, each $X^1$ and $X^2$ is, independently, selected from the group consisting of halides and $C_1$ to $C_5$ alkyl groups; each $X^1$ and $X^2$ is, independently, selected from the group consisting of chlorides, fluorides, methyl, ethyl, propyl and butyl groups; at least one of $R^6$, $R^7$, $R^8$, and $R^9$ and at least one of $R^1$, $R^2$, $R^3$, $R^4$, is a linear $C_3$ to $C_{20}$ substituted or unsubstituted hydrocarbyl group; each $R^2$, $R^3$, $R^4$, $R^6$, $R^7$, $R^8$, and $R^9$ is, independently, a linear $C_3$ to $C_{20}$ alkyl group; each $R^2$, $R^3$, $R^4$, $R^6$, $R^7$, $R^8$, and $R^9$ is, independently, selected from the group consisting of n-propyl, n-butyl, n-pentyl, and n-hexyl groups; each $R^a$ and $R^b$ is, independently, selected from the group consisting of phenyl and substituted phenyl groups.

The metallocene compounds that are particularly useful in this invention include one or more of:
diphenylsilylbis(n-propylcyclopentadienyl)hafnium$X^1X^2$,
diphenylsilylbis(n-butylcyclopentadienyl)hafnium$X^1X^2$,
diphenylsilylbis(n-pentylcyclopentadienyl)hafnium$X^1X^2$,
diphenylsilyl (n-propyl cyclopentadienyl)(n-butylcyclopentadienyl)hafnium$X^1X^2$,
diphenylsilylbis[(2-trimethylsilylethyl)cyclopentadienyl] hafnium$X^1X^2$,
dimethylsilylbis(n-propylcyclopentadienyl)hafnium$X^1X^2$,
dimethylsilylbis(n-butylcyclopentadienyl)hafnium$X^1X^2$,
dimethylsilylbis(n-pentylcyclopentadienyl)hafnium$X^1X^2$,
dimethylsilyl (n-propyl cyclopentadienyl)(n-butylcyclopentadienyl)hafnium$X^1X^2$, and
dimethylsilylbis[(2-trimethylsilylethyl)cyclopentadienyl] hafnium$X^1X^2$,
wherein each $X^1$ and $X^2$ is, independently, selected from the group consisting of chlorides, fluorides, methyl, ethyl, propyl, butyl groups and isomers thereof.

In a preferred embodiment in any of the processes described herein, one metallocene compound is used, e.g., the metallocene compounds are not different. For purposes of this invention, one metallocene compound is considered different from another if they differ by at least one atom. For example, "bisindenyl zirconium dichloride" is different from (indenyl)(2-methylindenyl) zirconium dichloride" which is different from "(indenyl)(2-methylindenyl) hafnium dichloride." Metallocene compounds that differ only by isomer are considered the same for purposes of this invention, e.g., rac-dimethylsilylbis(2-methyl 4-phenylindenyl)hafnium dimethyl is considered to be the same as meso-dimethylsilylbis(2-methyl 4-phenylindenyl)hafnium dimethyl.

In some embodiments, two or more different metallocene compounds are present in the catalyst system used herein. In some embodiments, two or more different metallocene compounds are present in the reaction zone where the process (es) described herein occur. When two transition metal compound based catalysts are used in one reactor as a mixed catalyst system, the two transition metal compounds are preferably chosen such that the two are compatible. A simple screening method such as by $^1$H or $^{13}$C NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination. If one or more transition metal compounds contain an $X^1$ or $X^2$ ligand which is not a hydride, hydrocarbyl, or substituted hydrocarbyl, then the alumoxane should be contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

Activators

The terms "cocatalyst" and "activator" are used herein interchangeably and are defined to be any compound which can activate any one of the metallocene compounds described above by converting the neutral metallocene compound to a catalytically active metallocene compound cation.

After the compounds described above have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprises a compound as described above and an activator such as alumoxane or a non-coordinating anion.

Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing non-coordinating or weakly coordinating anion.

Alumoxane Activators

In one embodiment, alumoxane activators are utilized as an activator in the catalyst system. Alumoxanes are generally oligomeric compounds containing —Al($R^1$)—O— subunits, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methylalumoxane (MMAO) cocatalyst type 3A (commercially available from Akzo Chemicals, Inc., under the trade name Modified Methylalumoxane type 3A, covered under U.S. Pat. No. 5,041,584).

When the activator is an alumoxane (modified or unmodified), some embodiments select the maximum amount of activator typically at up to a 5000-fold molar excess Al/M over the metallocene compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mol %, alternately the alumoxane is present at a molar ratio of aluminum to metallocene compound transition metal less than 500:1, preferably less than 300:1, preferably less than 100:1, preferably less than 1:1.

Non-Coordinating Anion Activators

A non-coordinating anion (NCA) is defined to mean an anion that either does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer, can displace it from the catalyst center. Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator and stoichiometric ionic activator can be used interchangeably. Likewise, the terms neutral stoichiometric activator and Lewis acid activator can be used interchangeably. The term non-coordinating anion includes neutral stoichiometric activators, ionic stoichiometric activators, ionic activators, and Lewis acid activators.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis(pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

The catalyst systems of this invention can include at least one non-coordinating anion (NCA) activator.

In a preferred embodiment, boron containing NCA activators represented by the formula below can be used:

wherein:
Z is (L-H) or a reducible Lewis acid; L is a neutral Lewis base; H is hydrogen;
(L-H) is a Bronsted acid; $A^{d-}$ is a boron containing non-coordinating anion having the charge d−; and
d is 1, 2, or 3.

The cation component, $Z_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $Z_d^+$ may also be a moiety such as silver, tropylium, carboniums, ferroceniums and mixtures, preferably carboniums and ferroceniums. Most preferably $Z_d^+$ is triphenyl carbonium. Preferred reducible Lewis acids can be any triaryl carbonium (where the aryl can be substituted or unsubstituted, such as those represented by the formula: ($Ar_3C^+$), where Ar is aryl or aryl substituted with a heteroatom, a $C_1$ to $C_{40}$ hydrocarbyl, or a substituted C1 to C40 hydrocarbyl), preferably the reducible Lewis acids in formula (14) above as "Z" include those represented by the formula: ($Ph_3C$), where Ph is a substituted or unsubstituted phenyl, preferably substituted with $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics, preferably Z is a triphenylcarbonium.

When $Z_d^+$ is the activating cation $(L-H)_d^+$, it is preferably a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiums from ethers such as dimethyl ether, diethyl ether, tetrahydrofuran, and dioxane, sulfoniums from thioethers, such as diethyl thioethers, tetrahydrothiophene, and mixtures thereof.

The anion component $A^{d-}$ includes those having the formula $[M^{k+}Q_n]^{d-}$ wherein k is 1, 2, or 3; n is 1, 2, 3, 4, 5, or 6 (preferably 1, 2, 3, or 4); n−k=d; M is an element selected from Group 13 of the Periodic Table of the Elements, preferably boron or aluminum, and Q is, independently, a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is incorporated herein by reference.

Illustrative, but not limiting examples of boron compounds, which may be used as an activating cocatalyst are the compounds described as (and particularly those specifically listed as) activators in U.S. Pat. No. 8,658,556, which is incorporated herein by reference.

Most preferably, the ionic stoichiometric activator $Z_d^+$ $(A^{d-})$ is one or more of N,N-dimethylanilinium tetra(perfluorophenyl)borate, N,N-dimethylanilinium tetrakis(perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Bulky activators are also useful herein as NCAs. "Bulky activator" as used herein refers to anionic activators represented by the formula:

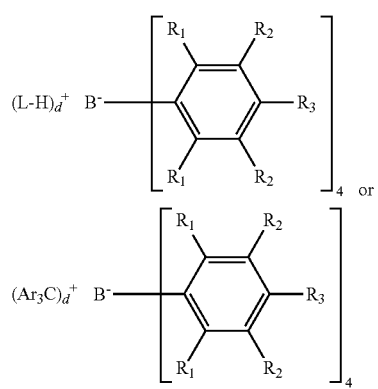

wherein:
each $R_1$ is, independently, a halide, preferably a fluoride;
Each Ar is a substituted or unsubstituted aryl group (preferably a substituted or unsubstituted phenyl), preferably substituted with $C_1$ to $C_{40}$ hydrocarbyls, preferably $C_1$ to $C_{20}$ alkyls or aromatics;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group);
wherein $R_2$ and $R_3$ can form one or more saturated or unsaturated, substituted or unsubstituted rings (preferably $R_2$ and $R_3$ form a perfluorinated phenyl ring); and
L is a neutral Lewis base; $(L-H)^+$ is a Bronsted acid;
d is 1, 2, or 3;
wherein the anion has a molecular weight of greater than 1020 g/mol; and
wherein at least three of the substituents on the B atom each have a molecular volume of greater than 250 cubic Å, alternately greater than 300 cubic Å, or alternately greater than 500 cubic Å.

Preferably $(Ar_3C)_d^+$ is $(Ph_3C)_d^+$, where Ph is a substituted or unsubstituted phenyl, preferably substituted with $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple 'Back of the Envelope' Method for Estimating the Densities and Molecular Volumes of Liquids and Solids," Journal of Chemical Education, November 1994, Vol. 71, No. 11, p. 962-964. Molecular volume (MV), in units of cubic A, is calculated using the formula: $MV=8.3V_S$, where $V_S$ is the scaled volume. $V_S$ is the sum of the relative volumes of the constituent atoms, and is calculated from the molecular formula of the substituent using the following table of relative volumes. For fused rings, the $V_S$ is decreased by 7.5% per fused ring.

| Element | Relative Volume |
| --- | --- |
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

For a list of particularly useful Bulky activators please see U.S. Pat. No. 8,658,556, which is incorporated herein by reference.

In another embodiment, one or more of the NCA activators is chosen from the activators described in U.S. Pat. No. 6,211,105.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4$$^-$], [Me$_3$NH$^+$][B(C$_6$F$_5$)$_4$$^-$]; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis (perfluoronaphthyl)borate, N,N-dialkylanilinium tetrakis (perfluoronaphthyl)borate, trialkylammonium tetrakis (perfluorobiphenyl)borate, N,N-dialkylanilinium tetrakis (perfluorobiphenyl)borate, tri alkyl ammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1, or alternately from 1:1 to 1000:1. A particularly useful range is from 0.5:1 to 10:1, preferably 1:1 to 5:1.

It is also within the scope of this invention that the metallocene compounds can be combined with combinations of alumoxanes and NCA's (see for example, U.S. Pat. Nos. 5,153,157; 5,453,410; EP 0 573 120 B1; WO 94/07928; and WO 95/14044; which discuss the use of an alumoxane in combination with an ionizing activator).

Chain Transfer Agents

Useful chain transfer agents are typically alkylalumoxanes, a compound represented by the formula AlR$_3$, ZnR$_2$ (where each R is, independently, a C$_1$-C$_8$ aliphatic radical, preferably methyl, ethyl, propyl, butyl, phenyl, hexyl octyl or an isomer thereof) or a combination thereof, such as diethyl zinc, methylalumoxane, trimethylaluminum, triisobutylaluminum, trioctylaluminum, or a combination thereof.

Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

Support Materials

In embodiments herein, the catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include Al$_2$O$_3$, ZrO$_2$, SiO$_2$, and combinations thereof, more preferably SiO$_2$, Al$_2$O$_3$, or SiO$_2$/Al$_2$O$_3$.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 μm. More preferably, the surface area of the support material is in the range of from about 50 to about 500 m$^2$/g, pore volume of from about 0.5 to about 3.5 cc/g and average particle size of from about 10 to about 200 μm. Most preferably, the surface area of the support material is in the range of from about 100 to about 400 m$^2$/g, pore volume of from about 0.8 to about 3.0 cc/g and average particle size is of from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 m$^2$/gm; pore volume of 1.65 cm$^3$/gm). Preferred silicas include those available under the tradenames of DAVISON 952 or DAVISON 955 by the Davison Chemical Division of W.R. Grace and Company. In other embodiments DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one metallocene compound and an activator.

The support material, having reactive surface groups, typically hydroxyl groups, is slurried in a non-polar solvent and the resulting slurry is contacted with a solution of a metallocene compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the metallocene compound is then contacted with the isolated support/activator. In some embodiments, the supported catalyst system is generated in situ. In an alternate embodiment, the slurry of the support material is first contacted with the metallocene compound for a period of time in the range of from about 0.5 hours to about 24 hours, from about 2 hours to about 16 hours, or from about 4 hours to about 8 hours. The slurry of the supported metallocene compound is then contacted with the activator solution.

The mixture of the metallocene, activator, and support is heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

This invention relates to a process to polymerize olefins comprising:

1) contacting olefin monomers with a catalyst system comprising an activator and a bis-cyclopentadienyl metallocene compound represented by the formula:

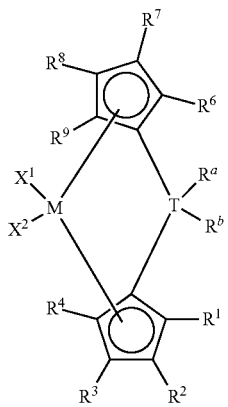

wherein:
M is Hf;
each $X^1$ and $X^2$ is, independently, a hydrocarbyl radical having from 1 to 20 carbon atoms, hydride, amide, alkoxide, sulfide, phosphide, halide, diene, amine, phosphine, ether, or $X^1$ and $X^2$ may form a part of a fused ring or a ring system;
each of $R^1$, $R^2$, $R^3$, $R^4$, $R^6$, $R^7$, $R^8$, and $R^9$ is, independently, hydrogen, halide, alkoxide or a $C_1$ to $C_{40}$ substituted or unsubstituted hydrocarbyl group, (preferably, each of $R^1$, $R^2$, $R^3$, $R^4$, $R^6$, $R^7$, $R^8$, and $R^9$ is, independently, a $C_1$ to $C_{20}$ substituted or unsubstituted hydrocarbyl group) provided that at least one of $R^1$, $R^2$, $R^3$, $R^4$, $R^6$, $R^7$, $R^8$, and $R^9$ is a linear $C_3$ to $C_{20}$ substituted or unsubstituted hydrocarbyl group (preferably at least one of $R^1$, $R^2$, $R^3$, $R^4$, $R^6$, $R^7$, $R^8$, and $R^9$ (preferably at least one of $R^2$, $R^3$, $R^7$ and $R^8$) is a $C_3$ to $C_{10}$ linear alkyl group;

T is a group 14 atom (preferably, silicon or germanium; more preferably, silicon);
each $R^a$ and $R^b$ is, independently, a $C_1$ to $C_{40}$ substituted or unsubstituted hydrocarbyl, (preferably a $C_1$ to $C_{20}$ substituted or unsubstituted alkyl, or a $C_6$ to $C_{20}$ substituted or unsubstituted aryl preferably, each $R^a$ and $R^b$ is, independently, selected from the group consisting of substituted or unsubstituted $C_1$ to $C_{12}$ alkyl groups, phenyl, and substituted phenyl groups);
wherein the bis-cyclopentadienyl metallocene compound generates hydrogen and the polymerization occurs in the presence of hydrogen, preferably at least 200 ppm hydrogen; and 2) obtaining a polymer having:
 a) an internal unsaturation of 50% or more, preferably 60% or more, preferably 70% or more;
 b) a melt index of 20 dg/min or less, preferably 1.0 dg/min or less; and
 c) a g'vis of 0.95 or more.

In embodiments herein, the invention relates to polymerization processes where monomer (such as ethylene), and optionally comonomer, are contacted with a catalyst system comprising an activator and at least one metallocene compound, as described above. The metallocene compound and activator may be combined in any order, and are combined typically prior to contacting with the monomer.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene, and isomers thereof. In a preferred embodiment of the invention, the monomer comprises propylene and optional comonomers comprising one or more ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and optional comonomers comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene.

In a preferred embodiment, one or more dienes are present in the polymer produced herein at up to 10 wt %, preferably at 0.00001 to 1.0 wt %, preferably 0.002 to 0.5 wt %, even more preferably 0.003 to 0.2 wt %, based upon the total weight of the composition. In some embodiments 500 ppm or less of diene is added to the polymerization, preferably 400 ppm or less, preferably 300 ppm or less. In other embodiments, at least 50 ppm of diene is added to the polymerization, or 100 ppm or more, or 150 ppm or more.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e., di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In some embodiments, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example, $C_4$ raffinate streams, and can therefore be substantially less expensive than pure 1-butene.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 vol % or more.) Alternately, no solvent or diluent is present or added in the reaction medium, (except for the small amounts used as the carrier for the catalyst system or other additives, or amounts typically found with the monomer; e.g., propane in propylene). In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins, which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt %, based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In some embodiments, hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In an alternate embodiment, the activity of the catalyst is at least 50 g/mmol/hour, preferably 500 or more g/mmol/hour, preferably 5000 or more g/mmol/hr, preferably 50,000 or more g/mmol/hr. In an alternate embodiment, the conversion of olefin monomer is at least 10%, based upon polymer yield and the weight of the monomer entering the reaction zone, preferably 20% or more, preferably 30% or more, preferably 50% or more, preferably 80% or more.

In a preferred embodiment, little or no alumoxane is used in the process to produce the polymers. Preferably, alumoxane is present at zero mol %, alternately the alumoxane is present at a molar ratio of aluminum to transition metal less than 500:1, preferably less than 300:1, preferably less than 100:1, preferably less than 1:1.

In a preferred embodiment, little or no scavenger is used in the process to produce the ethylene polymer. Preferably, scavenger (such as tri alkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the catalyst system used in the polymerization comprises no more than one metallocene compound. A "reaction zone" also referred to as a "polymerization zone" is a vessel where polymerization takes place, for example a batch reactor. When multiple reactors are used in either series or parallel configuration, each reactor is considered as a separate polymerization zone. For a multistage polymerization in both a batch reactor and a continuous reactor, each polymerization stage is considered as a separate polymerization zone. In a preferred embodiment, the polymerization occurs in one reaction zone. Room temperature is 23° C. unless otherwise noted.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

A solution polymerization as used herein means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng. Chem. Res., 2000, vol. 29, p. 4627.

A bulk polymerization as used herein means a polymerization process in which the monomers and/or comonomers being polymerized are used as a solvent or diluent using little or no inert solvent as a solvent or diluent. A small fraction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

Polyolefin Products with Internal Unsaturation Structures

This invention also relates to compositions of matter produced by the methods described herein.

In a preferred embodiment, the process described herein produces ethylene homopolymers or ethylene copolymers, such as ethylene-alphaolefin (preferably C3 to C20 alpha olefin) copolymers (preferably, such as ethylene-propylene, ethylene-butene, ethylene-hexene, or ethylene-octene copolymers) preferably having: a Mw/Mn of greater than 1 to 4 (preferably greater than 1 to 3).

Likewise, the processes of this invention produce homopolymers or copolymers of ethylene, where the ethylene copolymers preferably have from 0 mol % to 25 mol % (alternately from 0.5 mol % to 20 mol %, alternately from 1 mol % to 15 mol %, preferably from 3 mol % to 10 mol %) of one or more $C_3$ to $C_{20}$ olefin comonomer (preferably $C_3$ to $C_{12}$ alpha-olefin, preferably propylene, butene, hexene, octene, decene, dodecene, preferably propylene, butene, hexene, octene), or are copolymers of ethylene preferably having from 0 mol % to 25 mol % (alternately from 0.5 mol % to 20 mol %, alternately from 1 mol % to 15 mol %, preferably from 3 mol % to 10 mol %) of one or more of $C_3$ to $C_{20}$ olefin comonomer (preferably $C_3$ to $C_{12}$ alpha-olefin, preferably propylene, butene, hexene, octene, decene, dodecene, preferably ethylene, butene, hexene, or octene).

In a preferred embodiment, the monomer is ethylene and the comonomer is hexene, preferably from 1 mol % to 15 mol % hexene, alternately 1 mol % to 10 mol %.

Typically, the polymers produced herein have an Mw of 5,000 g/mol to 1,000,000 g/mol (preferably 25,000 g/mol to 750,000 g/mol, preferably 100,000 to 500,000 g/mol), and/or an Mw/Mn of greater than 1 to 40 (alternately 1.2 to 20, alternately 1.3 to 10, alternately 1.4 to 5, 1.5 to 4, alternately 1.5 to 3).

Typically, the polymers produced herein have a melt index (MI, also referred to as I2, determined according to ASTM D1238, 190° C., 2.16 kg load) of 20 dg/min or less, preferably 10 dg/min or less, preferably 5 dg/min or less, preferably 1.0 dg/min or less, preferably 0.9 dg/min or less, preferably 0.8 dg/min or less, preferably 0.7 dg/min or less, alternately from 0.01 dg/min to 20 dg/min, preferably from 0.01 dg/min to 10 dg/min, preferably from 0.05 dg/min to 5 dg/min, preferably from 0.1 dg/min to 1.0 dg/min, preferably from 0.2 dg/min to 0.9 dg/min.

In a preferred embodiment, the polymer produced herein has a unimodal or multimodal molecular weight distribution as determined by Gel Permeation Chromotography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versa).

Unless otherwise indicated Mw, Mn, and MWD are determined by GPC as described in US 2006/0173123, pp. 24-25, paragraphs [0334] to [0341].

In a preferred embodiment, the polymer produced herein has a composition distribution breadth index (CDBI) of 50% or more, preferably 60% or more, preferably 70% or more. CDBI is a measure of the composition distribution of monomer within the polymer chains and is measured by the procedure described in PCT publication WO 93/03093, published Feb. 18, 1993, specifically columns 7 and 8, as well as in Wild et al, J. Poly. Sci., Poly. Phys. Ed., 1982, Vol. 20, p. 441, and U.S. Pat. No. 5,008,204, including that fractions having a weight average molecular weight (Mw) below 15,000 are ignored when determining CDBI.

In a preferred embodiment the polymer produced herein has an internal unsaturation of 50% or more, preferably 60% or more, preferably 70% or more.

The polyolefins are unique with respect to higher levels of internal unsaturation structures, which even exceeds the amount of end groups theoretically possible for a polymer. Without wishing to bound by any particular theory, a possible internal unsaturation structures formation mechanism is disclosed at Macromolecules 2005, vol. 38, p. 6988, where internal vinylenes have been attributed to occur through the following mechanism.

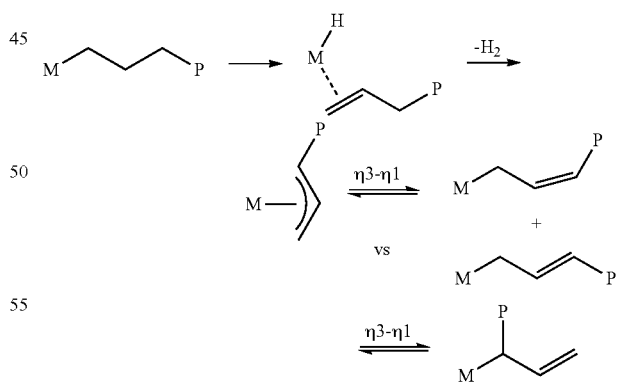

For purposes of this invention and the claims thereto, unsaturations in a polymer are determined by $^1$H NMR with reference to Macromolecules 2014, vol. 47, p. 3782 and Macromolecules 2005, vol. 38, p. 6988, but in event of conflict Macromolecules 2014, vol. 47, p. 3782 shall control. Peak assignments are determined referencing the solvent of tetrachloroethane-1,2 $d_2$ at 5.98 ppm. Specifically, percent internal unsaturation is determined by adding Vy1+

Vy2+trisubstituted olefins then dividing by total unsaturation. For example, for polymer 7.1 in Table 2, the percent internal unsaturation is [(0.22+0.02)/0.31]×100=77.4. Thus, the polymer produced in Example 7.1 has an internal unsaturation of 77.4%.

Advantageously, the polymers produced herein have an internal unsaturation of 50% or more, preferably 60% or more, preferably 70% or more, alternately from 50% to 90%, from 60% to 85%, from 60% to 80%.

Blends

In another embodiment, the polymer (preferably the polyethylene or polypropylene) produced herein, is combined with one or more additional polymers prior to being formed into a film, molded part, or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 wt % to 99 wt %, based upon the weight of the polymers in the blend, preferably 20 wt % to 95 wt %, even more preferably at least 30 wt % to 90 wt %, even more preferably at least 40 wt % to 90 wt %, even more preferably at least 50 wt % to 90 wt %, even more preferably at least 60 wt % to 90 wt %, and even more preferably at least 70 wt % to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Specifically, any of the foregoing polymers, such as the foregoing polypropylenes or blends thereof, may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular dye and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then, optionally, the combination could be oriented even further. Typically, the films are oriented in the Machine Direction (MD) at a ratio of up to 15, preferably between 5 and 7, and in the Transverse Direction (TD) at a ratio of up to 15, preferably 7 to 9. However, in another embodiment, the film is oriented to the same extent in both the MD and TD directions.

The films may vary in thickness depending on the intended application; however, films of a thickness from 1 μm to 50 μm are usually suitable. Films intended for packaging are usually from 10 μm to 50 μm thick. The thickness of the sealing layer is typically 0.2 μm to 50 μm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

In another embodiment, this invention relates to:
1. A process to polymerize olefins comprising:
1) contacting olefin monomers with a catalyst system comprising an activator and a bis-cyclopentadienyl metallocene compound represented by the formula:

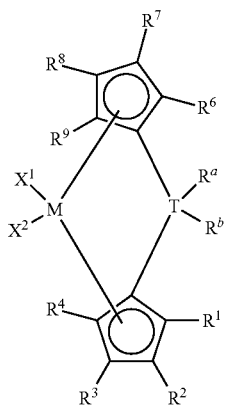

wherein:

M is Hf;

each $X^1$ and $X^2$ is independently, a hydrocarbyl radical having from 1 to 20 carbon atoms, hydride, amide, alkoxide, sulfide, phosphide, halide, diene, amine, phosphine, ether, or $X^1$ and $X^2$ may form a part of a fused ring or a ring system;

each of $R^1$, $R^2$, $R^3$, $R^4$, $R^6$, $R^7$, $R^8$, and $R^9$ is, independently, hydrogen, halide, alkoxide or a $C_1$ to $C_{40}$ (preferably $C_1$ to $C_{20}$) substituted or unsubstituted hydrocarbyl group, provided that at least one (preferably at least two) of $R^1$, $R^2$, $R^3$, $R^4$, $R^6$, $R^7$, $R^8$, and $R^9$ is a linear $C_3$ to $C_{20}$ substituted or unsubstituted hydrocarbyl group, alternately provided that at least one of $R^6$, $R^7$, $R^8$, and $R^9$ and at least one of $R^1$, $R^2$, $R^3$, $R^4$, is a linear $C_3$ to $C_{20}$ substituted or unsubstituted hydrocarbyl group;

T is a group 14 atom (preferably, silicon or germanium; more preferably, silicon);

each $R^a$ and $R^b$ is, independently, a $C_1$ to $C_{40}$ substituted or unsubstituted hydrocarbyl, (preferably a $C_1$ to $C_{20}$ substituted or unsubstituted alkyl, or a $C_6$ to $C_{20}$ substituted or unsubstituted aryl);

wherein the bis-cyclopentadienyl metallocene compound generates hydrogen and the polymerization occurs in the presence of hydrogen, preferably at least 200 ppm hydrogen;

2) obtaining a polymer having:
   a) an internal unsaturation of 50% or more;
   b) a melt index of 20 dg/min or less, preferably a melt index of 1.0 dg/min or less; and
   c) a g'vis of 0.95 or more.

2. The process of paragraph 1, wherein each $X^1$ and $X^2$ is, independently, selected from the group consisting of halides and $C_1$ to $C_5$ alkyl groups.

3. The process of paragraphs 1-2, wherein each $X^1$ and $X^2$ is, independently, selected from the group consisting of chlorides, fluorides, methyl, and ethyl groups.

4. The process of paragraphs 1-3, wherein at least one of $R^6$, $R^7$, $R^8$, and $R^9$ and at least one of $R^1$, $R^2$, $R^3$, $R^4$, is a linear $C_3$ to $C_{10}$ unsubstituted hydrocarbyl group.

5. The process of paragraphs 1-3, wherein each $R^2$, $R^3$, $R^4$, $R^6$, $R^7$, $R^8$, and $R^9$ is, independently, a linear $C_3$ to $C_{20}$ alkyl group, preferably an n-propyl, n-butyl, n-pentyl, and n-hexyl group.

6. The process of paragraphs 1-3, wherein at least one of $R^2$ and $R^3$ and at least one of $R^7$ and $R^8$ is, independently, selected from the group consisting of n-propyl, n-butyl, n-pentyl, and n-hexyl groups.

7. The process of paragraphs 1-6, wherein each $R^a$ and $R^b$ is, independently, selected from the group consisting of C1 to C20 alkyls, phenyl, and substituted phenyl groups.

8. The process of paragraphs 1-7, wherein the metallocene compound comprises one or more of: diphenylsilylbis(n-propylcyclopentadienyl)hafnium $X^1X^2$, diphenylsilylbis(n-butylcyclopentadienyl)hafnium$X^1X^2$, diphenylsilylbis(n-pentylcyclopentadienyl)hafnium$X^1X^2$, diphenylsilyl (n-propyl cyclopentadienyl)(n-butylcyclopentadienyl) hafnium$X^1X^2$, diphenylsilylbis[(2-trimethylsilylethyl)cyclopentadienyl]hafnium$X^1X^2$, dimethylsilylbis(n-propylcyclopentadienyl)hafnium$X^1X^2$, dimethylsilylbis(n-butylcyclopentadienyl)hafnium$X^1X^2$, dimethylsilylbis(n-pentylcyclopentadienyl)hafnium$X^1X^2$, dimethylsilyl (n-propyl cyclopentadienyl)(n-butylcyclopentadienyl) hafnium$X^1X^2$, dimethylsilylbis[(2-trimethylsilylethyl)cyclopentadienyl]hafnium$X^1X^2$, wherein each $X^1$ and $X^2$ is, independently, selected from the group consisting of chlorides, fluorides, methyl, ethyl, propyl, and butyl groups.

9. The process of paragraphs 1-8, wherein the activator comprises alumoxane.

10. The process of paragraph 9, wherein the alumoxane is present at a molar ratio of aluminum to transition metal of the metallocene compound of 100:1 or more.

11. The process of paragraphs 1-10, wherein the activator comprises a non-coordinating anion activator.

12. The process of paragraphs 1-11, wherein the activator is represented by the formula:

$$(Z)_d^+(A^{d-})$$

wherein Z is (L-H) or a reducible Lewis Acid, L is a neutral Lewis base; H is hydrogen; $(L-H)^+$ is a Bronsted acid; $A^{d-}$ is a non-coordinating anion having the charge d−; and d is an integer from 1 to 3.

13. The process of claim paragraphs 1-12, wherein the activator is one or more of: N,N-dimethylanilinium tetrakis (perfluoronaphthyl)borate, N,N-dimethylanilinium tetrakis (perfluorobiphenyl)borate, N,N-dimethylanilinium tetrakis (perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph3C+][B(C6F5)4-], [Me3NH+][B(C6F5)4-], 1-(4-(tris(pentafluorophenyl)borate)-2,3,5,6-tetrafluorophenyl)pyrrolidinium, tetrakis(pentafluorophenyl)borate, 4-(tris(pentafluorophenyl)borate)-2,3,5,6-tetrafluoropyridine, triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis (perfluorobiphenyl)borate, triphenylcarbenium tetrakis(3,5-bis(trifluoromethyl)phenyl)borate), trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl) borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl)borate, N,N-dialkylanilinium tetrakis(3,5-bis(trifluoromethyl) phenyl)borate, N,N-dialkyl-(2,4,6-trimethylanilinium) tetrakis(3,5-bis(trifluoromethyl)phenyl)borate, di-(i-propyl) ammonium tetrakis(pentafluorophenyl)borate, wherein alkyl is methyl, ethyl, propyl, n-butyl, sec-butyl, or t-butyl.

14. The process of claim paragraphs 1-13, wherein the olefin monomer comprises ethylene.

15. The process of paragraphs 1-14, wherein the catalyst system is supported on an inert support material.

16. The process of paragraphs 1-15, wherein the catalyst system is supported on a support material selected from the group consisting of talc, inorganic oxides, zeolites, clays, organoclays and mixtures thereof.

17. The process of claim paragraphs 1-16, wherein step 1) occurs at a temperature of from about 0° C. to about 300° C., at a pressure in the range of from about 0.35 MPa to about 10 MPa, and at a time of up to 300 minutes.

18. A catalyst system comprising an activator and a bis-cyclopentadienyl metallocene compound represented by the formula:

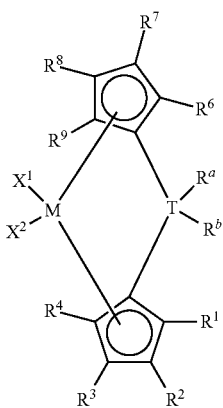

wherein:
M is Hf;
each $X^1$ and $X^2$ is, independently, a hydrocarbyl radical having from 1 to 20 carbon atoms, hydride, amide, alkoxide, sulfide, phosphide, halide, diene, amine, phosphine, ether, or $X^1$ and $X^2$ may form a part of a fused ring or a ring system; each of $R^1$, $R^2$, $R^3$, $R^4$, $R^6$, $R^7$, $R^8$, and $R^9$ is, independently, hydrogen, halide, alkoxide or a $C_1$ to $C_{40}$ (preferably $C_1$ to $C_{20}$) substituted or unsubstituted hydrocarbyl group, provided that at least one, preferably at least two, of $R^1$, $R^2$, $R^3$, $R^4$, $R^6$, $R^7$, $R^8$, and $R^9$, is a linear $C_3$ to $C_{20}$ substituted or unsubstituted hydrocarbyl group;
T is a group 14 atom (preferably, silicon or germanium; more preferably, silicon);
each $R^a$ and $R^b$ is, independently, a $C_1$ to $C_{40}$ substituted or unsubstituted hydrocarbyl, (preferably a $C_1$ to $C_{20}$ substituted or unsubstituted alkyl, a $C_6$ to $C_{20}$ substituted or unsubstituted aryl).

19. The catalyst system of paragraph 18, wherein each $X^1$ and $X^2$ is, independently, selected from the group consisting of halides and $C_1$ to $C_5$ alkyl groups.

20. The catalyst system of paragraphs 18-19, wherein each $X^1$ and $X^2$ is, independently, selected from the group consisting of chlorides, fluorides, methyl, and ethyl groups.

21. The catalyst system of paragraphs 18-20, wherein each $R^2$, $R^3$, $R^4$, $R^6$, $R^7$, $R^8$, and $R^9$ is, independently, a linear $C_3$ to $C_{20}$ alkyl group.

22. The catalyst system of paragraphs 18-21, wherein at least one of $R^2$ and $R^3$, $R^4$ and at least one of $R^7$ and $R^8$ is, independently, selected from the group consisting of n-propyl, n-butyl, n-pentyl, and n-hexyl groups.

23. The catalyst system of paragraphs 18-22, wherein each $R^a$ and $R^b$ is, independently, selected from the group consisting of substituted or unsubstituted C1 to C20 alkyls, phenyl, and substituted phenyl groups.

24. The catalyst system of paragraphs 18-23, wherein the metallocene compound comprises one or more of:
diphenylsilylbis(n-propylcyclopentadienyl)hafnium $X^1X^2$,
diphenylsilylbis(n-butylcyclopentadienyl)hafnium$X^1X^2$,
diphenylsilylbis(n-pentylcyclopentadienyl)hafnium$X^1X^2$,
diphenylsilyl (n-propyl cyclopentadienyl)(n-butylcyclopentadienyl)hafnium$X^1X^2$,
diphenylsilylbis[(2-trimethylsilylethyl)cyclopentadienyl] hafnium$X^1X^2$,
dimethylsilylbis(n-propylcyclopentadienyl)hafnium$X^1X^2$,
dimethylsilylbis(n-butylcyclopentadienyl)hafnium$X^1X^2$,
dimethylsilylbis(n-pentylcyclopentadienyl)hafnium$X^1X^2$,
dimethylsilyl (n-propyl cyclopentadienyl)(n-butylcyclopentadienyl)hafnium$X^1X^2$,
dimethylsilylbis[(2-trimethylsilylethyl)cyclopentadienyl] hafnium$X^1X^2$,
wherein each $X^1$ and $X^2$ is, independently, selected from the group consisting of chlorides, fluorides, methyl, ethyl, propyl, and butyl groups.

25. An ethylene polymer having: a) an internal unsaturation of 50% or more; b) a melt index of 20 dg/min or less, preferably 1.0 dg/min or less; and c) a g'vis of 0.95 or more.

26. A film comprising the polymer of paragraph 25.

27. A tie layer in a film comprising the polymer of paragraph 25.

Test Methods
$^1$H NMR

$^1$H NMR data was collected at 120° C. using a 10 mm CryoProbe with a Bruker spectrometer at a $^1$H frequency of 600 MHz (available from Bruker Corporation, United Kingdom). Data were recorded using a maximum pulse width of 45°, 5 seconds between pulses and signal averaging 512 transients. Samples were prepared by dissolving 80 mg of sample in 3 mL of solvent heated at 140° C. For purposes of this invention and the claims thereto, unsaturations in a polymer are determined by $^1$H NMR with reference to Macromolecules, 2014, vol. 47, p. 3782 and Macromolecules, 2005, vol. 38, p. 6988, but in event of conflict Macromolecules, 2014, vol. 47, p. 3782, shall control. Peak assignments are determined referencing the solvent of tetrachloroethane-1,2 $d_2$ at 5.98 ppm.

GPC-DRI

Mn (GPC), Mw, Mz and g'(vis) were determined using a Gel Permeation Chromatography (GPC) method using a High Temperature Size Exclusion Chromatograph (SEC, either from Waters Corporation, Milford, Mass. or Polymer Laboratories (now part of Varian Inc., available from Agilent Technologies)), equipped with a differential refractive index detector (DRI). Experimental details are described in: T. Sun, P. Brant, R. R. Chance, and W. W. Graessley, Macromolecules, Volume 34, Number 19, 6812-6820, (2001), and references therein. Three Polymer Laboratories PLgel 10 mm Mixed-B columns are used. The nominal flow rate was 0.5 cm$^3$/min and the nominal injection volume is 300 μL. The various transfer lines, columns, and differential refractometer (the DRI detector) were contained in an oven maintained at 135° C. Solvent for the SEC experiment was prepared by dissolving 6 grams of butylated hydroxy toluene as an antioxidant in 4 liters of Aldrich reagent grade 1, 2, 4 trichlorobenzene (TCB). The TCB mixture was then filtered through a 0.7 μm glass pre-filter and subsequently through a 0.1 μm Teflon filter. The TCB was then degassed with an online degasser before entering the SEC. Polymer solutions were prepared by placing dry polymer in a glass container, adding the desired amount of TCB, then heating the mixture at 160° C. with continuous agitation for about 2 hours. All quantities were measured gravimetrically. The TCB densities used to express the polymer concentration in mass/volume units were 1.463 g/mL at room temperature and 1.324 g/mL at 135° C. The injection concentration was from 1.0 mg/mL to 2.0 mg/mL, with lower concentrations being used for higher molecular weight samples. Prior to running each sample, the DRI detector and the injector were purged. Flow rate in the apparatus was then increased to 0.5 mL/minute and the DRI was allowed to stabilize for 8 to 9 hours before injecting the first sample. The concentration, c, at each point in the chromatogram was calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 135° C. and λ=690 nm. For purposes of this invention and the claims thereto, (dn/dc)=0.104 for propylene polymers and ethylene polymers and 0.1 otherwise. Units of parameters used throughout this description of the SEC method were: concentration was expressed in g/cm³, molecular weight was expressed in g/mol, and intrinsic viscosity was expressed in dL/g.

The resultant polymer is analyzed by GPC to determine the molecular weight and by DRI to determine percent of 1-hexene incorporation.

Polymers produced by the processes of this invention also have a g'(vis) of greater than 0.95 (preferably greater than 0.96, preferably greater than 0.98, preferably greater than 0.99, and, optionally, preferably less than or equal to 1.0). The branching index (g'(vis)) is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits, wherein $[\eta]_i$ is the intrinsic viscosity over the chromatographic slices, i.

The branching index g'(vis) is defined as:

$$g'vis = \frac{[\eta]_{avg}}{kM_v^\alpha}$$

where, for purpose of this invention and claims thereto, α=0.695 and k=0.000579 for linear ethylene polymers, α=0.705 k=0.000262 for linear propylene polymers, and α=0.695 and k=0.000181 for linear butene polymers. $M_V$ is the viscosity-average molecular weight based on molecular weights determined by LS analysis. See Macromolecules, 2001, 34, pp. 6812-6820 and Macromolecules, 2005, 38, pp. 7181-7183, for guidance on selecting a linear standard having similar molecular weight and comonomer content, and determining k coefficients and α exponents.

All molecular weights are weight average unless otherwise noted. All molecular weights are reported in g/mol unless otherwise noted.

Melt index (MI) also referred to as I2, reported in g/10 min, is determined according to ASTM D1238, 190° C., 2.16 kg load.

High load melt index (HLMI) also referred to as I21, reported in g/10 min, is determined according to ASTM D1238, 190° C., 21.6 kg load.

Melt index ratio (MIR) is MI divided by HLMI as determined by ASTM D1238.

Density is determined according to ASTM D1505.

Bulk density is measured by quickly transferring (in 10 seconds) the sample powder into a graduated cylinder which overflows when exactly 100 cc is reached. No further powder is added at this point. The rate of powder addition prevents settling within the cylinder. The weight of the powder is divided by 100 cc to give the density.

EXAMPLES

All reactions were carried out under inert atmosphere, preferably nitrogen, unless otherwise stated. All solvents were obtained from Sigma Aldrich Co. and dried before use over 3 A molecular sieves (also obtained from Sigma Aldrich), unless otherwise stated. Bis(n-propyl-cyclopentadienyl)hafnium dimethyl was purchased from Boulder. ¹H NMR measurements for catalyst syntheses were recorded on a 400 Mz Bruker spectrometer.

The following abbreviations used herein: Catalyst 1 is dimethylsilylbis (3-n-propyl cyclopentadienyl) hafnium dimethyl; Catalyst 2 is diphenylsilylbis (3-n-propyl cyclopentadienyl) hafnium dimethyl; Catalyst 3 is (1,3-MeBuCp)₂ZrCl₂; MAO is methylalumoxane; and TIBAL is triisobutylaluminum. MAO is obtained from Albemarle (Baton Rouge, La.) and TIBAL is obtained from Sigma Aldrich Co. (St. Louis, Mo.), and both were used as received, unless otherwise stated.

Example 1: Synthesis of rac/meso Me₂Si(3-n-PropylCp)₂HfMe₂ (Catalyst 1)

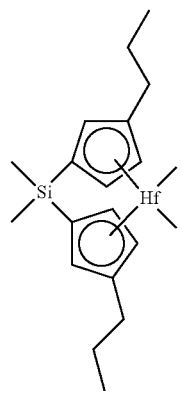

A solution of dimethylsilyl dichloride (3.0 g) in THF was cooled in a freezer to −25° C. To this was added 5.3 g of n-propylcyclopentadiene and stirred for 12 h. The solvent was removed in vacuo to give an off white solid. Pentane was added and the slurry stirred for 1 h. The slurry was then filtered through a glass frit and evaporated to give 6.3 g of a yellow oil.

The resulting dimethylsilylbis(n-propylcyclopentadiene) was dissolved in THF and cooled to −25° C. Next, 18.4 mL of a 2.5M solution of n-butyllithium in hexane was added slowly to the solution. The reaction was allowed to stir 12 h after which the solvent was removed in vacuo. The reaction was slurried in pentane and the solvent was filtered off to give an off-white powder (4.7 g), which was dried in vacuo.

The 4.7 g of lithium diphenylsilylbis(n-propylcyclopentadienide) was added to a slurry of 5.2 g of $HfCl_4$ in diethyl ether that had been cooled to −25° C. After stirring for 12 h the reaction was filtered through a glass frit and dried in vacuo to give a light orange oil. This was dissolved in pentane, filtered and the filtrate dried in vacuo to give a light orange oil (4.1 g).

The resulting dimethylsilylbis(n-propylcyclopentadienyl) hafnium dichloride was dissolved in THF and cooled to −25° C. Methyl magnesium bromide (6.6 mL) was then added slowly and left to stir for 12 h. The solvent was then removed in vacuo to a dark orange oil that was then dissolved in pentane. The reaction was filtered and the solvent removed in vacuo to give 3.95 g of a dark orange viscous oil of rac/meso dimethylsilylbis(3-n-propylcyclopentadienyl) hafnium dimethyl. $^1$H NMR (400 MHz, $CDCl_2$) δ 6.45 (1H, t), 6.42 (1H, t), 5.59 (1H, t), 5.48 (1H, t), 5.37 (1H, t), 5.29 (1H, t), 2.64-2.49 (4H, m), 1.66-1.60 (4H, m), 0.98 (6H, t), 0.46 (6H, t), −0.74 (6H, t).

Example 2: Synthesis of rac/meso $Ph_2Si(3$-n-PropylCp$)_2HfMe_2$ (Catalyst 2)

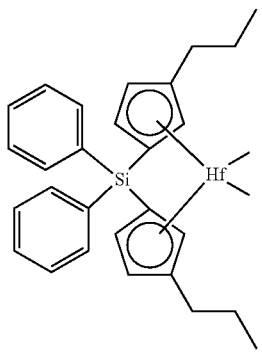

A solution of diphenylsilyl dichloride (5.0 g) in THF was cooled to −25° C. To this solution 4.5 g of n-propyl cylopentadiene was added and stirred for 12 h. The solvent was then removed in vacuo to give a light orange oil. This oil was dissolved in pentane, filtered through a glass frit, evaporated in vacuo to give 7.1 g of orange oil.

Next, 5.0 g of the resulting diphenylsilyl(bis-n-propylcyclopentadiene) was dissolved in THF and cooled to −25° C. Then 10.0 mL of a 2.5M solution of n-butyllithium in hexane was added slowly to the stirring solution. This was allowed to stir for 6 h before removing the solvent in vacuo. Next, the reaction was slurried in pentane and the solvent filtered off. The resulting white powder (1.94 g) was dried in vacuo.

The 1.94 g of diphenylsilyl(bis-lithium n-propyl cyclopentadiene) was added to a slurry of 1.7 g of $HfCl_4(OEt_2)_2$ in diethyl ether that was cooled to −25° C. After stirring for 12 h the reaction was filtered and then dried in vacuo. The resulting orange oil was dissolved in pentane, filtered through a glass frit and the filtrate dried in vacuo to a viscous yellow oil (1.8 g).

The resulting diphenylsilyl(bis-n-propylcyclopentadienyl) hafnium dichloride (1.8 g) was dissolved in diethyl ether and cooled to −25° C. Methyl magnesium bromide (1.9 mL) was then added slowly and left to stir for 12 h. The solvent was then removed in vacuo to an orange oil then dissolved in pentane. The reaction was then filtered and the pentane removed in vacuo to give 1.7 g of an orange viscous oil of rac/meso diphenylsilyl(bis-3-n-propylcyclopentadienyl) hafnium dimethyl. $^1$H NMR (400 MHz, $CDCl_2$) δ 7.92 (4H, t), 7.48 (6H, t), 6.57 (2H, d), 5.75 (1H, s), 5.67 (1H, s), 5.54 (1H, s), 5.50 (1H, s), 2.68-2.54 (4H, m), 1.71 (4H, m), 1.05 (6H, t), −0.67 (6H, t).

Example 3: Preparation of Support 3.1 Preparation of sMAO-a

Davison 948 silica (40.7 g), calcined at 600° C. for 2 hours, was slurried in 200 mL of toluene. MAO (71.4 g of a 30% wt toluene solution, 351.1 mmol of Al) was added slowly to the slurry. The slurry was then heated to 80° C. and stirred for 1 hr. The slurry was filtered, washed three times with 70 mL of toluene and once with pentane. The solid was dried under vacuum overnight to give a 60.7 g amount of free flowing white solid.

3.2 Preparation of sMAO-b

Fluorided D948 silica preparation: 1.18 g $(NH_4)_2SiF_6$ was dissolved in 7.00 g water in a 20 ml glass vial, 50 g raw Grace D948 silica and 200 g of toluene were combined in a 250 ml celstir. Under vigorous stirring, the aqueous solution of $(NH_4)_2SiF_6$ was added via a syringe to the toluene slurry. The mixture was allowed to stir at room temperature for 2.5 h. The milky slurry was filtered through a 500 ml Optichem disposable polyethylene frit (40 micron), rinsed with 200 g pentane for three times, then dried in air overnight to yield a white, free-flowing solid. The solid was transferred into a tube furnace, and was heated to 200° C. under constant nitrogen flow (temperature program: 25° C./h ramped to 150° C.; held at 150° C. for 4 hours; 50° C./h ramped to 200° C.; held at 200° C. for 4 hours; cooled down to room temperature). 46 g of fluorided D948 was collected after the calcination. Calculated F-loading: 0.8 mmol/g (F-loading=mmol of F/gram of added raw silica).

sMAO-b preparation: MAO (37.6 g of 30% wt in toluene) was added to a 250 ml celstir along with 100 mL of toluene. 29.9 g fluorided D948 silica was prepared in the previous step and was added to the slurry in 5 g increments. The reaction was stirred for 10 minutes at room temperature and was then heated to 100° C. for 3 hours. The solid was filtered, washed twice with 80 mL of toluene, washed twice with pentane, and dried under vacuum overnight. 39.6 g of free flowing white solid was collected.

Example 4: Preparation of Supported Catalysts 4.1 Supported Catalyst A

Rac/meso $Ph_2Si(3$-nPrCp$)_2HfMe_2$ (0.0284 g, 0.0471 mmol) was dissolved in 7 milliliters of toluene and added to a Celstir™ flask. A 1.18 gram amount of sMAO-a was added as a solid all at once to the Celstir™ flask and washed down with 7 milliliters of toluene. The slurry was stirred at room temperature for 1 hour. The solid was filtered, washed three times with 15 milliliters of toluene, and washed twice with pentane. The solid was dried under vacuum to give a 1.09 gram amount of off-white powder.

4.2 Supported Catalyst B

Rac/meso $Me_2Si(3$-nPrCp$)_2HfMe_2$ (0.018 g, 0.0378 mmol) was dissolved in 3 milliliters of toluene and added to a Celstir™ flask. A 0.949 gram amount of sMAO-a was added as a slurry in 15 mls of toluene all at once to the Celstir™ flask and washed down with 7 milliliters of toluene. The slurry was stirred at room temperature for 1 hour.

The solid was filtered, washed three times with 15 milliliters of toluene, and washed twice with pentane. The solid was dried under vacuum to give a 0.885 gram amount of off-white powder.

4.3 Supported Catalyst C 1,3-MeBuCp$_2$ZrCl$_2$ was supported on silica (about 4 µmol/g) according to the general procedure described in U.S. Pat. No. 6,180,736.

4.4 Supported Catalyst D 20.0 mg Catalyst 1 (dimethylsilylbis (3-n-propyl cyclopentadienyl) hafnium dimethyl, 42 µmop was dissolved in 2.07 g of toluene in a 20 ml glass vial. 0.51 g sMAO-a was slurried in 2.0 g of toluene in a 20 ml glass vial. 1.0 gram of the Catalyst 1/toluene solution was added to the sMAO-a/toluene slurry via a pipette. The glass vial was capped with a Teflon-lined cap and vortexed at room temperature for 90 min. The resulting slurry was filtered through a 18 mL polyethylene frit (10 micron), and rinsed with 3 g toluene for 3 times, followed by 2 g of pentane for 3 times. The collected solid was dried under vacuum for 40 min. 0.488 g of supported Catalyst 1 was collected. Calculated catalyst loading: 39 µmol/g (catalyst loading=µmol of catalyst/gram of added sMAO-a).

4.5 Supported Catalyst E 20.0 mg Catalyst 1 (42 µmop was dissolved in 2.07 g of toluene in a 20 ml glass vial. 0.4920 g sMAO-b was slurried in 2.0 g of toluene in a 20 ml glass vial. 1.00 gram of the Catalyst 1/toluene solution was added to the sMAO-b/toluene slurry via a pipette. The glass vial was capped with a Teflon-lined cap and vortexed at room temperature for 90 min. The resulting slurry was filtered through a 18 mL polyethylene frit (10 micron), and rinsed with 3 g toluene for 3 times, followed by 2 g of pentane for 3 times. The collected solid was dried under vacuum for 40 min. 0.4700 g of supported Catalyst 1 was collected. Calculated catalyst loading: 41 µmol/g (catalyst loading=µmol of catalyst/gram of added sMAO-b).

4.6 Supported Catalyst F

Catalyst 2 (diphenylsilylbis (3-n-propyl cyclopentadienyl) hafnium dimethyl, 23.8 mg, 39 µmol) was combined with 1.00 gram of sMAO-b and 4.0 gram of toluene in a 20 ml glass vial in the dry box. The glass vial was capped with a Teflon-lined cap and vortexed at room temperature for 90 min. The resulting slurry was filtered through a 18 mL polyethylene frit (10 micron), and rinsed with 3 g toluene for 3 times, followed by 2 g of pentane for 3 times. The collected solid was dried under vacuum for 40 min. Calculated catalyst loading: 39 µmol/g (catalyst loading=µmol of catalyst/gram of added sMAO-b).

4.7 Supported Catalyst G (n-prCp)$_2$HfMe$_2$ was supported on sMao-a (40 µmol/g) according to the general procedure described in U.S. Pat. No. 6,180,736.

Monomers

Polymerization grade ethylene was used and further purified by passing it through a series of columns: 2250 ml Oxyclear cylinder from Labclear (Oakland, Calif.), followed by a 2250 cc column packed with dried 3 Å mole sieves purchased from Aldrich Chemical Company (St. Louis, Mich.), two 500 cc columns packed with dried 5 Å mole sieves purchased from Aldrich Chemical Company, one 500 cc column packed with ALCOA Selexsorb CD (7×14 mesh) purchased from Coastal Chemical Company (Abbeville, La.), and one 500 cc column packed with ALCOA Selexsorb COS (7×14 mesh) purchased from Coastal Chemical Company.

Polymerization grade 1-hexanes were further purified by passing it through a series of columns: two 500 cc Oxyclear cylinders from Labclear followed by two 500 cc columns packed with dried 3 Å mole sieves purchased from Aldrich Chemical Company and two 500 cc columns packed with dried 5 Å mole sieves purchased from Aldrich Chemical Company and used.

1-Hexene was obtained from Sigma Aldrich (St. Louis, Mo.) and was dried over NaK amalgam.

Example 5: Slurry Phase Polymerization of Ethylene and 1-Hexene

Into a 1 L stainless steel autoclave reactor was added scavenger (TIBAL, as a 1-hexane solution) followed by 500 mls of isobutane. Ethylene was added (180 psi) and the reactor was heated to 80° C. with the stirring rate set at 750 rpm. The supported catalyst system was then added by a short nitrogen purge through a small stainless steel bomb attached securely to the reactor. Ethylene was maintained at the initial pressure throughout the polymerization. The polymerization was allowed to proceed for a set time at which time the reactor was cooled and excess pressure vented into the hood. The solid resin was transferred into an appropriate glass vessel and dried at 80° C. in a vacuum oven for at least 2 h. Process conditions and characterization results for the resins are summarized in Table 1.

As shown in Table 1, Catalyst 2 can be used to produce a polymer having a higher Mw, which is more than 100,000 g/mol. The lower MIR values obtained for the resins indicates little or no long chain branching (LCB). The lack of LCB was further supported by the GPC trace which yielded a g'vis value of approximately 1.0.

TABLE 1

Slurry Phase Polymerization of Ethylene and 1-Hexene

| Example | Supported Catalyst | Hexene in feed | MI dg/min | MIR | Mw g/mol | Mn g/mol | Mw/Mn | Hexene wt % | Activity gP/gsup. Cat. | g' (vis) |
|---|---|---|---|---|---|---|---|---|---|---|
| 5.1 | A | 10 ml | 0.566 | 18 | 150,000 | 48,800 | 3.07 | 4.86 | 1328 | 1.004 |
| 5.2 | B | 10 ml | 2.03 | 19 | 93,700 | 38,400 | 2.44 | 3.96 | 1668 | 1.016 |
| 5.3 | C | 10 ml | 0.245 | 18.9 | 178,000 | 71,500 | 2.5 | 1.74 | 653 | |

[1] H NMR analysis of the polymers indicates that there is significant internal unsaturation structures as noted by triplet like peak (possibly two overlapping triplets) in the vinylene region of the $^1$H NMR spectrum that can be attributed to internal cis/trans olefins. References to be used for internal vinylenes assignments are the following: Macromolecules 2005, vol. 38, p. 6988 and Macromolecules 2014, vol. 47, p. 3782.

TABLE 2

Unsaturations per 1000 Carbons in E-H Copolymers

| E-H Copolymer | Ex 7.1 | Ex 5.1 | Ex. 5.2 | Ex 5.3 |
|---|---|---|---|---|
| Vy1 and Vy2 (cis and trans) | 0.22 | 0.16 | 0.22 | 00.06 |
| Vy5 | 0.05 | 0.07 | 0.07 | 00.04 |
| Trisubstituted olefins | 0.02 | 0.01 | 0.03 | 00.02 |
| Vinyls (terminal) | 0.00 | 0.02 | 0.02 | 0.06 |
| Vinylidenes (terminal) | 0.02 | 0.01 | 0.01 | 0.02 |
| Total unsaturation | 0.31 | 0.27 | 0.35 | 0.2 |
| % internal unsaturation (Vy1 + Vy2 + Trisub/total unsaturation) | 77.40% | 62.90% | 71.40% | 40.0% |

Example 6: High Throughput Polymerizations of Ethylene and 1-Hexene

Ethylene and 1-hexene copolymerizations were carried out in a parallel pressure reactor, as generally described in U.S. Pat. Nos. 6,306,658; 6,455,316; 6,489,168; WO 00/09255; and Murphy et al., J. Am. Chem. Soc., 2003, vol. 125, pp. 4306-4317, each of which is incorporated herein by reference for US purposes. Although the specific quantities, temperatures, solvents, reactants, reactant ratios, pressures, and other variables are frequently changed from one polymerization run to the next, the following describes a typical polymerization performed in a parallel pressure reactor. A pre-weighed glass vial insert and disposable stirring paddle were fitted to each reaction vessel of the reactor.

The reactor was prepared as described above, and then purged with ethylene. Isohexane, 1-hexene and TIBAL were added via syringe at room temperature and atmospheric pressure. The reactor was then brought to process temperature (85° C.) and charged with ethylene to process pressure (130 psig=896 kPa) while stirring at 800 RPM. A series of supported catalysts shown in Table 3, as prepared in Example 4 (100 μL of a 3 mg/mL toluene slurry, unless indicated otherwise), were added via syringe with the reactor at process conditions. TIBAL was used as 200 μL of a 20 mmol/L in isohexane solution. Ethylene was allowed to enter (through the use of computer controlled solenoid valves) the autoclaves during polymerization to maintain reactor gauge pressure (+/−2 psig). Reactor temperature was monitored and typically maintained within +/−1° C. Polymerizations were halted by addition of approximately 50 psi $O_2$/Ar (5 mol % $O_2$) gas mixture to the autoclaves for approximately 30 seconds. The polymerizations were quenched after a predetermined cumulative amount of ethylene had been added or for a maximum of 300 minutes polymerization time. The reactors were cooled and vented. The polymer was isolated after the solvent was removed in-vacuo. Catalyst activity is calculated as kilograms of polymer per mol transition metal compound per hour of reaction time (kg/mol·hr). Characterization results of the resins are summarized in Table 3.

TABLE 3

High Throughput Polymerization of Ethylene and 1-Hexene

| Supported Catalyst | $H_2$ level (ppm) | mol % C6 in feed | Activity (kg/mol · h) | Mw (kg/mol) | PDI (Mw/Mn) | wt % C6 |
|---|---|---|---|---|---|---|
| C | 0 | 6 | 18193 | 461 | 2.0 | 2.4 |
|   | 300 | 6 | 21070 | 266 | 1.9 | 2.0 |
| D | 0 | 6 | 32359 | 314 | 2.2 | 3.8 |
| E | 0 | 6 | 33790 | 332 | 2.0 | 3.8 |
|   | 0 | 11 | 39081 | 433 | 2.0 | 5.4 |
|   | 300 | 6 | 35610 | 275 | 2.0 | 3.3 |
| F | 0 | 6 | 35011 | 394 | 2.1 | 4.2 |
|   | 0 | 11 | 40497 | 452 | 2.1 | 5.4 |
|   | 300 | 6 | 36697 | 278 | 1.9 | 4.4 |

As can be seen from Table 3, the present catalyst system shows an improved incorporation of hexene comonomer, and higher Mw more than 100,000 g/mol. In addition, fluorided catalyst system (sMao-b) exhibits higher activity and percent of comonomer incorporation.

Example 7: Gas Phase Polymerization of Ethylene and 1-Hexene

Polymerization was performed in a 7 foot tall gas-phase fluidized bed reactor with a 4 foot tall 6' diameter body and a 3 foot tall 10' diameter expanded section. Cycle and feed gases were fed into the reactor body through a perforated distributor plate, and the reactor was controlled at 300 psi and 70 mol % ethylene. Reactor temperature was maintained by heating the cycle gas. Supported catalyst was fed as a 10 wt % slurry in Sono Jell® from Sonneborn (Parsippany, N.J.). The slurry was delivered to the reactor by nitrogen and isopentane feeds in a ⅛" diameter catalyst probe. Polymer was collected from the reactor as necessary to maintain the desired bed weight. Average process conditions are shown in Table 4.

TABLE 4

| Example | 7.1 | 7.2 | 7.3 |
|---|---|---|---|
| Supported Catalyst cat name | B | A | G |
| Temperature (° C.) | 185 | 185 | 185 |
| Pressure (psi) | 300 | 299 | 295 |
| Ethylene (mole %) | 69.8 | 69.7 | 70.1 |
| Hydrogen (ppm) | 323 | 349 | 300 |
| Hydrogen Flow (sccm) | 4.98 | 5.24 | 13.14 |
| $H_2/C_2$ Flow Ratio ((sccm $H_2$)/(g/hr $C_2$)) | 0.003 | 0.003 | 0.007 |
| Hexene (mole %) | 0.64 | 0.62 | 1.03 |
| Bed Weight (g) | 1596 | 2894 | 1574 |
| Residence Time (hr) | 3.8 | 7.5 | 2.9 |
| Cycle Gas Velocity (ft/s) | 1.58 | 1.54 | 1.58 |
| Production Rate (g/hr) | 423 | 384 | 550 |
| Activity ($g_{poly}/g_{supported\ cat}$) | 1915 | 2207 | 2224 |
| Catalyst Slurry Feed (cc/hr) | 2.5 | 2 | 2.8 |
| MI (g/10 min) | 0.88 | 0.62 | 0.74 |
| HLMI (g/10 min) | 17.11 | 13.09 | 13.76 |
| MIR | 19.37 | 21.19 | 18.65 |
| Density (g/cm³) | 0.9196 | 0.9227 | 0.9162 |
| Bulk Density (g/cc) | 0.3480 | 0.3997 | 0.3689 |
| g'(vis) | 1.024 | | |
| $N_2$ Cat. Probe Feed (cc/min) | 6000 | 6000 | 6000 |
| $iC_5$ Cat. Probe Feed (g/min) | 1 | 1 | 1 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A polymerizing catalyst system present in an olefin polymerization reaction in the presence of at least 200 ppm of hydrogen, said catalyst system comprising an activator and a bis-cyclopentadienyl metallocene compound represented by the formula:

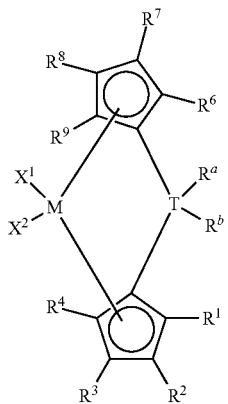

wherein:
M is Hf;
each $X^1$ and $X^2$ is, independently, a hydrocarbyl radical having from 1 to 20 carbon atoms, hydride, amide, alkoxide, sulfide, phosphide, halide, diene, amine, phosphine, ether, or $X^1$ and $X^2$ optionally form a part of a fused ring or a ring system;
each of $R^1$, $R^2$, $R^3$, $R^4$, $R^6$, $R^7$, $R^8$, and $R^9$ is, independently, hydrogen, halide, alkoxide or a $C_1$ to $C_{40}$ substituted or unsubstituted hydrocarbyl group, provided that at least one of $R^1$, $R^2$, $R^3$, $R^4$, $R^6$, $R^7$, $R^8$, and $R^9$ is a linear $C_3$ to $C_{20}$ substituted or unsubstituted hydrocarbyl group;
T is a group 14 atom; and
each $R^a$ and $R^b$ is, independently, a $C_1$ to $C_{40}$ substituted or unsubstituted hydrocarbyl, wherein: the metallocene catalyst, as activated in the catalyst system, produces a polymer having an internal unsaturation of 50% or more when olefin is polymerized with said polymerizing catalyst system.

2. The polymerizing catalyst system of claim 1, wherein each $X^1$ and $X^2$ is, independently, a halide or a $C_1$ to $C_5$ alkyl group.

3. The polymerizing catalyst system of claim 1, wherein each $R^a$ and $R^b$ is, independently, a $C_6$ to $C_{20}$ substituted or unsubstituted aryl.

4. The polymerizing catalyst system of claim 1, wherein each $R^2$, $R^3$, $R^4$, $R^6$, $R^7$, $R^8$, and $R^9$ is, independently, a linear $C_3$ to $C_{20}$ alkyl group.

5. The polymerizing catalyst system of claim 1, wherein each $R^2$, $R^3$, $R^4$, $R^6$, $R^7$, $R^8$, and $R^9$ is, independently, a n-propyl, n-butyl, n-pentyl, or n-hexyl group.

6. The polymerizing catalyst system of claim 1, wherein at least one of $R^7$ and $R^8$ and at least one of $R^2$ and $R^3$ is, independently, a n-propyl, n-butyl, n-pentyl, or n-hexyl group and each $R^a$ and $R^b$ is, independently, a C1 to C20 alkyl group, phenyl, or a substituted phenyl group.

7. The polymerizing catalyst system of claim 1, wherein the metallocene compound comprises one or more of:
diphenylsilylbis(n-propylcyclopentadienyl)hafnium$X^1X^2$,
diphenylsilylbis(n-butylcyclopentadienyl)hafnium$X^1X^2$,
diphenylsilylbis(n-pentylcyclopentadienyl)hafnium$X^1X^2$,
diphenylsilyl (n-propyl cyclopentadienyl)(n-butyl cyclopentadienyl)hafnium$X^1X^2$,
diphenylsilylbis[(2-trimethylsilylethyl)cyclopentadienyl]hafnium$X^1X^2$,
diphenylsilylbis(2-n-propylindenyl)hafnium$X^1X^2$,
diphenylsilylbis(2-n-butylindenyl)hafnium$X^1X^2$,
dimethylsilylbis(n-propylcyclopentadienyl)hafnium$X^1X^2$,
dimethylsilylbis(n-butylcyclopentadienyl)hafnium$X^1X^2$,
dimethylsilylbis(n-pentylcyclopentadienyl)hafnium$X^1X^2$,
dimethylsilyl (n-propyl cyclopentadienyl)(n-butyl cyclopentadienyl)hafnium$X^1X^2$, and
dimethylsilylbis[(2-trimethylsilylethyl)cyclopentadienyl]hafnium$X^1X^2$,
wherein each $X^1$ and $X^2$ is, independently, selected from the group consisting of chlorides, fluorides, methyl, ethyl, propyl, and butyl groups.

8. The polymerizing catalyst system of claim 1, wherein the polymer is an ethylene polymer having: a) an internal unsaturation of 50% or more; b) a melt index of 1.0 dg/min or less; and c) a g'vis of 0.95 or more.

9. The polymerizing catalyst system of claim 1, wherein the polymer is an ethylene polymer having: a) an internal unsaturation of 50% or more; b) a melt index of 20 dg/min or less; and c) a g'vis of 0.95 or more.

10. The polymerizing catalyst system of claim 1, wherein one metallocene compound is present.

11. The polymerizing catalyst system of claim 1, further comprising chain transfer agent.

12. The polymerizing catalyst system of claim 1, further comprising chain transfer agent represented by the formula $AlR_3$ or $ZnR_2$ (where each R is, independently, a $C_1$-$C_8$ aliphatic radical.

13. The polymerizing catalyst system of claim 1, further comprising chain transfer agent represented by the formula $AlR_3$, $ZnR_2$ (where each R is, independently, methyl, ethyl, propyl, butyl, pentyl, hexyl octyl or an isomer thereof) or a combination thereof.

14. The polymerizing catalyst system of claim 1, further comprising scavengers or co-activators.

15. The polymerizing catalyst system of claim 1, further comprising trimethyl aluminum, triethylaluminum, triisobutylaluminum, tri-n-hexylaluminum, tri-n-octylaluminum, or diethyl zinc.

16. The polymerizing catalyst system of claim 8, wherein the polymer has an internal unsaturation of 70% or more.

17. The polymerizing catalyst system of claim 9, wherein the polymer has an internal unsaturation of 70% or more.

18. The polymerizing catalyst system of claim 8, wherein the polymer has g'(vis) of greater than 0.98.

19. The polymerizing catalyst system of claim 9, wherein the polymer has g'(vis) of greater than 0.98.

20. The polymerizing catalyst system of claim 1, further comprising support.

21. The polymerizing catalyst system of claim 1, further comprising a support comprising a Group 2, 4, 13, and 14 metal oxide.

22. The polymerizing catalyst system of claim 1, further comprising a support comprising silica, alumina, or a mixture thereof.

23. The polymerizing catalyst system of claim 1, wherein a polymer having an internal unsaturation of 70% or more is obtained when olefin is polymerized with said polymerizing catalyst system.

24. The polymerizing catalyst system of claim 1, wherein at least 400 ppm of hydrogen is present.

25. The polymerizing catalyst system of claim 1, wherein at least 600 ppm of hydrogen is present.

26. The polymerizing catalyst system of claim 1, wherein the catalyst system is supported on silica, and a polymer having an internal unsaturation of 70% or more is obtained when olefin is polymerized with said polymerizing catalyst system.

27. The polymerizing catalyst system of claim 1, wherein a polymer having an internal unsaturation of 60 to 90% is obtained when olefin is polymerized with said polymerizing catalyst system.

28. The polymerizing catalyst system of claim 1, wherein each $R^a$ and $R^b$ comprises a phenyl or substituted phenyl group.

29. The polymerizing catalyst system of claim 1, wherein the activator comprises alumoxane and/or a non-coordinating anion activator.

30. The polymerizing catalyst system of claim 1, wherein the activator comprises alumoxane present at a molar ratio of aluminum to transition metal of the metallocene compound of 100:1 or more.

31. The polymerizing catalyst system of claim 1, wherein the activator is represented by the formula:

wherein Z is (L-H) or a reducible Lewis Acid, L is a neutral Lewis base; H is hydrogen; $(L-H)^+$ is a Bronsted acid; $A^{d-}$ is a non-coordinating anion having the charge d−; and d is an integer from 1 to 3.

32. The polymerizing catalyst system of claim 1, wherein the activator is one or more of:
N,N-dimethylanilinium tetrakis(perfluoronaphthyl)borate,
N,N-dimethylanilinium tetrakis(perfluorobiphenyl)borate,
N,N-dimethylanilinium tetrakis(perfluorophenyl)borate,
N,N-dimethylanilinium tetrakis(3,5-bis(trifluoromethyl)phenyl)borate,
triphenylcarbenium tetrakis(perfluoronaphthyl)borate,
triphenylcarbenium tetrakis(perfluorobiphenyl)borate,
triphenylcarbenium tetrakis(3,5-bis(trifluoromethyl)phenyl)borate,
triphenylcarbenium tetrakis(perfluorophenyl)borate,
[[Me$_3$NH$^+$][B(C$_6$F$_5$)$_4$$^-$],
1-(4-(tris(pentafluorophenyl)borate)-2,3,5,6-tetrafluorophenyl)pyrrolidinium, tetrakis(pentafluorophenyl)borate,
4-(tris(pentafluorophenyl)borate)-2,3,5,6-tetrafluoropyridine,
triphenylcarbenium tetraphenylborate,
triphenylcarbenium tetrakis(pentafluorophenyl)borate,
triphenylcarbenium tetrakis-(2,3,4,6-tetrafluorophenyl)borate,
triphenylcarbenium tetrakis(perfluoronaphthyl)borate,
triphenylcarbenium tetrakis(perfluorobiphenyl)borate,
triphenylcarbeniumtetrakis(3,5-bis(trifluoromethyl)phenyl)borate),
trialkylammonium tetrakis(pentafluorophenyl)borate,
N,N-dialkylanilinium tetrakis(pentafluorophenyl)borate,
N,N-dimethyl-(2,4,6-trimethylanilinium) tetrakis(pentafluorophenyl)borate,
trialkylammonium tetrakis-(2,3,4,6-tetrafluorophenyl)borate,
N,N-dialkylanilinium tetrakis-(2,3,4,6-tetrafluorophenyl)borate,
trialkylammonium tetrakis(perfluoronaphthyl)borate,
N,N-dialkylanilinium tetrakis(perfluoronaphthyl)borate,
trialkylammonium tetrakis(perfluorobiphenyl)borate,
N,N-dialkylanilinium tetrakis(perfluorobiphenyl)borate,
trialkylammonium tetrakis(3,5-bis(trifluoromethyl)phenyl)borate,
N,N-dialkylanilinium tetrakis(3,5-bis(trifluoromethyl)phenyl)borate,
N,N-dialkyl-(2,4,6-trimethylanilinium)tetrakis(3,5-bis(trifluoromethyl)phenyl)borate, and
di-(i-propyl)ammonium tetrakis(pentafluorophenyl)borate,
wherein alkyl is methyl, ethyl, propyl, n-butyl, sec-butyl, or t-butyl.

33. The polymerizing catalyst system of claim 1, wherein the catalyst system is supported on silica.

34. The polymerizing catalyst system of claim 1, wherein the catalyst system is supported on support material selected from the group consisting of talc, inorganic oxides, zeolites, clays, organoclays and mixtures thereof.

* * * * *